United States Patent [19]

Powell-Jones et al.

[11] Patent Number: 5,977,056
[45] Date of Patent: Nov. 2, 1999

[54] TREATMENT OF THROMBOTIC EVENTS

[75] Inventors: Christopher Powell-Jones, Ffairfach; Roy T. Sawyer, Trapp; Asgar Electricwala; Anthony Atkinson, both of Salisbury, all of United Kingdom

[73] Assignee: Biopharm (UK) Limited, Hendy, United Kingdom

[21] Appl. No.: 08/624,760

[22] Filed: Mar. 27, 1996

Related U.S. Application Data

[63] Continuation of application No. 08/433,955, May 4, 1995, abandoned, which is a continuation of application No. 07/834,528, Feb. 6, 1992, abandoned, which is a continuation of application No. PCT/GB91/00549, Apr. 8, 1991.

[30] Foreign Application Priority Data

Apr. 20, 1990 [GB] United Kingdom ............... 9008863
Apr. 8, 1991 [GB] United Kingdom ............... 9007879

[51] Int. Cl.$^6$ .................. A01N 37/18; A61K 38/00; A61K 38/48; C07K 1/00
[52] U.S. Cl. .................. 514/2; 514/44; 424/94.63; 424/350; 424/337; 424/520; 530/355; 530/855
[58] Field of Search .................. 514/2, 44; 424/94.63, 424/350, 337, 520, 355, 855; 530/355, 855

[56] References Cited

U.S. PATENT DOCUMENTS 4,390,630  6/1983  Sawyer et al. .................. 435/226
4,832,849  5/1989  Cardin .................. 210/635

FOREIGN PATENT DOCUMENTS

WO 90/05143  5/1990  WIPO.

OTHER PUBLICATIONS

Malinconico et al., "Fabrinogen degradation by hementin, a fibrinogenolytic anticoagulant from the salivary glands of the leech *Haementeria ghilanii*," *J. Lab. Clin. Med.,* vol. 104, No. 5, (Nov. 1984).

Munro et al., "Effects of Hementin on Fibrinogen Mediated Platelet Aggregation/Deaggregation In Vitro," *Platelets,* 2:167–168 (1991).

Yasuda et al., "Lysis of Plasminogen Activator–Resistant Platelet–Rich Coronary Artery Thrombus With Combined Bolus Injection of Recombinant Tissue–Type Plasminogen Activator and Antiplatelet GPIIb/IIIa Antibody," *JACC,* vol. 16, No. 7, 1728–35, (Dec. 1990).

Forth et al., "Pharmakotherapie von Störungen der Blutgerinnung," *Antikoagulantien, Aggregationshemmer, Fibrinolytika Und Hemmstoffe Der Fibrinolyse,* 437–456.

Edwin L. Madison et al. (1989) *Nature,* vol. 339, pp. 721–724.

Scott M. Malinconico et al. (1984) *J. Lab. Clin. Med.,* vol. 104(5), pp. 842–854.

Nancy E. Kirschbaum et al. (1990) *J. Biol. Chem.,* vol. 265(23), pp. 13669–13676.

R.T. Sawyer et al. (1991) *Blood Coagulation and Fibrinolysis,* vol. 2, pp. 153–159.

J.K. Swadesh et al. (1990) *J. Chromatography,* vol. 502, pp. 359–369.

Blankenship et al. (1990) *Biochem. Biophys. Res. Comm.,* vol. 166, pp. 1384–1389.

Muller et al. (Eds) 1981. in "Neurobiology of the Leech", Cold Spring Harbor Laboratory, N.Y. pp. 7–26.

Kramer et al. 1981. J Comp Physiol A Sensneural Behav Physiol. 144(4):435–448—(Biosis Abstract only–AN 73068936).

Malinconico et al. 1984. J. Lab. Clin. Med. 103(1):44–58.
Mao et al. 1988. Biochemistry 27:8170–8173.

*Primary Examiner*—Brian R. Stanton
*Assistant Examiner*—Jill D. Martin
*Attorney, Agent, or Firm*—Darby & Darby

[57] ABSTRACT

A method for preventing the formation of platelet-rich clots or thrombus, and for deaggregating platelet-rich clots or thrombus, using hementin, a polypeptide derived from leech salivary glands. Hementin may be administered for this purpose in a pharmaceutically acceptable carrier or excipient, with or without additional anticoagulants such as hirudin, hirudin analogues, or an inhibitor of factor Xa.

8 Claims, 17 Drawing Sheets

TREATMENT OF THROMBOTIC EVENTS

This is a continuation of application Ser. No. 08/433,955, filed May 4, 1995, now abandoned, which is a continuation of application Ser. No. 07/834,528, filed Feb. 6, 1992 now abandoned, which is a continuation of PCT appln. GB91/00549 filed on Apr. 8, 1991.

FIELD OF THE INVENTION

This invention relates to methods and materials for prevention and treatment of life threatening blood clots (thrombi) which occur in patients suffering from thrombotic diseases such as heart disease and stroke.

BACKGROUND OF THE INVENTION

Thrombosis is the disease process which culminates in the formation of a blood clot (thrombus or embolism) which blocks (occludes) a blood vessel supplying blood to a vital organ, such as the heart or brain. Unless these thrombi are treated, the result can be death by heart attack (myocardial infarction), pulmonary embolism or stroke. In addition to these life threatening forms of thrombosis, there is a plethora of minor thrombotic events and conditions which are mainly due to inappropriate formation of clots in the vasculature. Examples of such events are deep vein thrombosis and, more seriously, the thrombosis caused by bacterial infection resulting in septic shock. The mechanism by which thrombosis occurs is very complex and not completely understood but is believed in some cases to be initiated by the exposure of a diseased part of the blood vessel wall (atheromatous lesion) to the normal healing process of blood clotting (haemostasis) which involves the accumulation at the site of injury of blood components such as platelets and fibrin deposits.

At some point, unless treatment is given, such a thrombus grows sufficiently large either to occlude the vessel in which it is formed or it breaks off and travels in the blood stream until it blocks a blood vessel of smaller diameter (this phenomenon being known as embolism).

At present treatment for thrombotic disease is largely confined to two well-known forms of therapy, as follows:
1. prevention of clot formation with anti-coagulants, and
2. cleavage of a fibrin clot (by fibrinolysis or thrombolysis) by administration of a plasminogen activator such as tissue plasminogen activator (TPA) in order to activate the production of plasmin from plasminogen.

However, a material has not as yet been identified which can, in a therapeutically effective amount, specifically dissolve or deaggregate platelet aggregates, which often occlude blood vessels in the manner described above. (A therapeutically effective amount is an amount which would be acceptable to a patient, with acceptably low risk of adverse side effects, such as general proteolysis.)

The linkages between the platelets present in platelet aggregates generally comprise fibrinogen, but there is no direct correlation such that materials having fibrinogenolytic properties are necessarily capable of platelet aggregate deaggregation. Thrombolytic agents without the ability to deaggregate platelet aggregates have been identified and it is known that many fibrinogenolytic enzymes (although capable of dissolving fibrinogen) cannot deaggregate platelet aggregates. For example, plasminogen activators such as streptokinase or urokinase do not deaggregate platelet aggregates and neither do N-terminal fibrinogenases such as thrombin or fibrinogenases isolated from snake venom.

The differing roles, and hence modes of action, of hementin and plasminogen activators, in respectively breaking up fibrin clots and platelet aggregates, are illustrated in FIG. 1. Plasminogen activators promote the conversion of plasminogen to plasmin which acts on fibrin clots; in contrast hementin has been found to act on the fibrinogen linkages of the platelet aggregates so as to cause subsequent deaggregation of the aggregates by preferential cleavage.

Deaggregation of platelet aggregates was thought to be impossible by treatment of the aggregates with a specific enzyme (such as a fibrinogenase) in a therapeutically effective manner. TPA is known in excessively high concentrations (i.e. in substantial excess of a therapeutically effective amount) to promote deaggregation of platelet aggregates by proteolysis by plasmin of fibrinogen-crosslinked platelets. However, TPA does not selectively deaggregate platelet aggregates; furthermore it has an adverse effect on other clotting factors in the circulation system (such as Factor X) and can cause lysis of haemostatic plugs which arise in repair areas in the vasculature. It has been suggested that this non-specific action of plasminogen activators may be the cause of haemorrhaging which often occurs with such thrombolytic agents. The action of TPA is analogous to that of an unspecific protease and is not specific to the fibrinogen linkages of the platelet aggregates.

Another factor precluding the use of TPA to deaggregate platelet aggregates in vivo is that it would be necessary to administer an unacceptably high level to a patient for the administered TPA to have the desired therapeutic effect. Furthermore, TPA is inhibited by plasma and it would therefore be necessary to administer the TPA as a continuous perfusion for it to retain its deaggregating activity against platelet aggregates.

Various materials having activity in mammalian cardiovascular systems are known to be present in leech secretions; amongst these is hementin, a fibrinolytic enzyme derived from leeches of the order Rhynchobdellida, such as the leech species *Haementeria ghilianii*. Hementin, and the isolation thereof, is described in U.S. Pat. No. 4,390,630.

The fibrinogenolytic activity of hementin is described by Malinconico S. M.; Katz J. B. and Budzynski A. Z. in "Fibrinogen degradation by hementin—a fibrinogenolytic anticoagulant from the salivary glands of the leech *Haementeria ghilianii*", in J. Lab. Clin. Med. 1984; 104(5) pp842–854. There is no hint or suggestion in either this article, or in the abovementioned U.S. Pat. No. 4,390,630, of hementin having the unique ability relative to other fibrinogenolytic enzymes, to deaggregate platelet aggregates.

SUMMARY OF THE INVENTION

We have now discovered an unexpected property for compositions comprising hementin, which is the ability in vivo of such compositions in therapeutically effective amounts, to specifically dissolve platelet aggregates (including platelet-rich clots) via fibrinogen cleavage, to the exclusion of other coagulation factors and blood clots.

DETAILED DESCRIPTION OF THE INVENTION

Figure 1A:
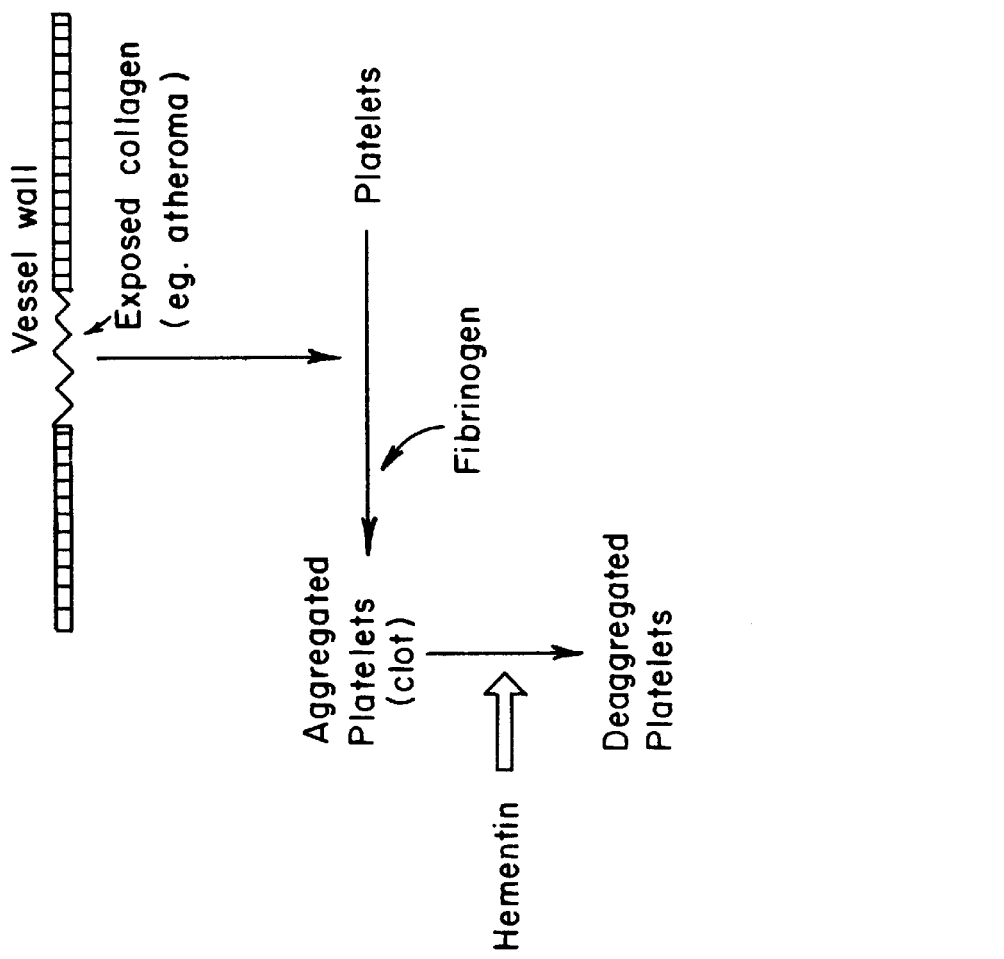
FIG. 1 shows a schematic representation of the formation of fibrin and platelet clots.
Figure 1B:
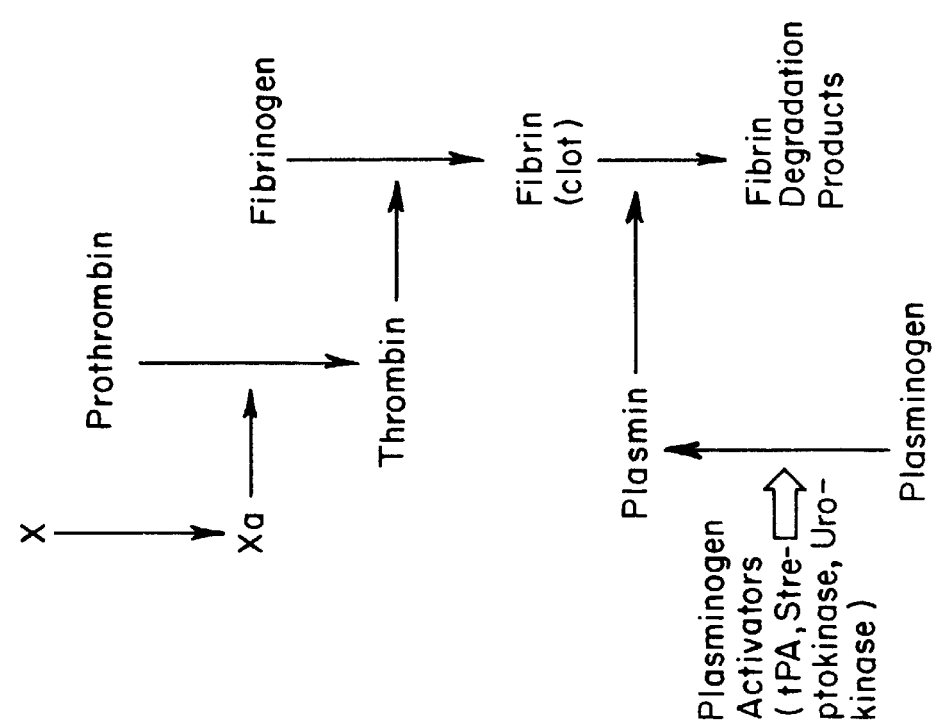

According to a first aspect of the invention therefore, there is provided a method of treatment of thrombotic events, which comprises administering to an animal patient (such as a human animal) at a locus having a clot which predominantly, by volume, comprises platelet aggregates, a therapeutically effective amount of a composition comprising hementin in such an amount and in such a manner as to deaggregate said aggregates.

The precise mechanism by which hementin deaggregates platelet aggregates and hence dissolves platelet rich clots appears to be unique. All other fibrinogenolytic enzymes cleave preferentially either:

1. at the COOH-terminal of the exposed Aa chain of fibrinogen, e.g. plasmin and some snake venoms (this exposed Aa chain is also susceptible to enzyme attack by general proteases such as trypsin), or
2. at the $NH_2$-terminal of the fibrinogen molecule e.g. thrombin and some snake venoms, which are primarily concerned with removal of fibrinopeptide A and/or fibrinopeptide B (or similar short peptide fragments), the removal of which usually results in the formation of a component which is still capable of polymerising and hence forming a clot predominantly comprising fibrin.

Hementin is the only known enzyme which cleaves first through all the three chains (Alpha, Beta and Gamma) in the connector region between the D and E domains (Kirschbaum, N. E. and Budzynski, A. Z. 1990. "A unique proteolytic fragment of human fibrinogen containing the Aa COOH-terminal domain of the native molecule"; J. Biol. Chem 265: 13669–13676) and which (in a therapeutically effective amount) can subsequently deaggregate platelet aggregates. It has been postulated that cleaving at this site is the most accessible and most effective for breaking the bivalent nature of fibrinogen bound to platelets (Sawyer, R. T., Powell-Jones, C. and Munro, R. 1991. The biological function of hementin in the proboscis of the Amazon leech *Haementeria ghilianii*; Blood coagulation and Fibrinolysis Vol.2, pp153–159). There is no hint or suggestion of the primary structure of hementin in the above mentioned patents or papers.

According to a second aspect of the present invention, there is provided a method of treatment of thrombotic events, which method comprises administering to an animal patient (such as a human patient) at a locus having a clot predominantly (by volume) comprising platelet aggregates, a therapeutically effective amount of a material capable of preferentially cleaving between the D and E domains of the fibrinogen linkage of said platelet aggregates, in such an amount and in such a manner as to deaggregate said aggregates.

The platelet aggregates treated by the method according to the invention may be blood clots which might otherwise block blood vessels thereby causing illness by heart attack, pulmonary embolism or stroke or other major or minor manifestation of impaired blood supply.

Patients suffering from pulmonary embolism typically experience accelerated Erythrocyte Sedimentation Rate (ESR). Administration of a composition comprising hementin to such patients, according to the method of the present invention, has now been shown to reduce accelerated ESR. Furthermore, the action of hementin-containing compositions to reduce ESR also demonstrates that accelerated ESR is in some way related to erythrocyte interaction with fibrinogen. Hementin can therefore serve as a diagnostic index to the degree of erythrocyte interaction with fibrinogen in individual patients. Additionally, it has also been found that, where increased plasma fibrinogen affects blood viscosity, hementin compositions can be used therapeutically to reduce the viscosity.

A further advantageous property of hementin is that its in vivo activity in deaggregating platelet aggregates is significantly enhanced relative to its in vitro activity. This is completely opposite to the relative general activities of TPA in vivo and in vitro; TPA has a much lower general activity in vivo compared to in vitro due to inhibition in vivo by plasma.

The composition used in treating such thrombotic events may be derived directly from leech tissue or leech secretions of leeches of the order Rhynchobdellida (for example, from salivary glands of *Haementeria ghilianii*), or optionally, it may be further purified (for example, to essentially pure hementin, which is characterised by having a single primary protein peak and specific activity greater than 1000 u/mg protein). Alternatively, it may be derived indirectly by genetic manipulation and replication techniques from such tissue or secretions (and, as explained hereinafter, it is only now that we have elucuidated the amino acid sequence of hementin that such manipulation and replication techniques has become possible). Typically, cloned material is indirectly derived from leech tissue or leech secretions of leeches of the order Rhynchobdellida and expressed from a bacterial host in which the hementin is replicated.

Previously, only a short amino acid sequence of hementin was known, which was insufficient to allow the construction and replication of a unique oligonucleotide probe. The reported sequence for the first 10 amino acids at the N-terminal end of hementin from the anterior salivary glands was reported to be as follows (Swadesh, J. K., Huang, T. Y. and Budzynski, A. Z. 1990. "Purification and characterisation of hementin, a fibrinogenolytic protease from the leech *Haementeria ghilianii*"; J. Chromatography 502: 359–369):

```
       1              5                  10
    thr-thr-leu-thr-glu-pro-glu-pro-asp-leu-
```

We have now further elucidated the amino acid sequence of hementin which makes possible replication thereof.

We have determined the N-terminal sequence of hementin, isolated from either the anterior or posterior gland to be:

```
Thr Thr Leu Thr Glu Pro Glu Pro Xaa Leu Thr Xaa Leu Xaa Phe
              5                   10                  15

Val Xaa Xaa Val Xaa Xaa Xaa Met Pro Ile Phe Xaa Met Ala Xaa
                20              25                  30

Ala Xaa Ser Gln Ile Xaa Xaa Xaa Phe
                35

1            5                10               15
thr-thr-leu-thr-glu-pro-glu-pro-phe-leu-thr-tyr-leu-thr-phe-val- 20
arg(or lys)-ile-val-asn-(or lys)-val(or leu)-glu-met-pro-ile-phe- 30              35            39
val-met-ala-thr-ala-asn-ser-gln-ile-thr-ser-thr-phe- (for the posterior).
```

We have also elucidated an internal amino acid sequence of anterior gland hementin to be

```
1             5                10              15
   *  *  *  *  *      *   *
gly-tyr-thr-asn-tyr-ala-lys-phe-leu-asp-tyr-leu-pro-val-glu-arg- 20
gly-ile-pro-leu
```

Portions of this sequence in positions 2–6 and 8–9 (indicated by asterisks), respectively, correspond to the sequence reported by Swadesh et al (1990. J. Chromatography 502: pp. 359–369) and designated a contaminating peptide in hementin purification. The sequence was: glu-val-try-thr-asn-tyr-ala-ser-phe-leu- Our sequence probably does not correspond to a contaminating peptide; the sequence may result from acid hydrolysis of asn-gly bond within the hementin molecule.

DNA base sequences coding for any of the above amino acid sequences can be extrapolated or determined by standard techniques; the present invention therefore comprises a DNA base sequence coding for any of the above new amino acid sequences.

The composition comprising hementin may be derived by homogenising dissected salivary glands (typically from leeches of the order Rhynchobdellida, such as *Haementeria ghilianii* or *Haementeria officinalis,* or other related species) in a suitable aqueous solvent, and purifying the active ingredients using a sequence of chromatographic operations.

There is therefore provided by the present invention a method of isolating a material capable of dissolving preformed platelet aggregates, which method comprises:

(a) in the case where the starting material is leech tissue, homogenising at least the salivary glands of leeches of the order Rhynchobdellida in a Hepes buffer;

(b) purification of the homogenate of step (a), or secretions from the salivary glands of leeches of the order Rhynchobdellida in a Hepes buffer, or cloned hementin expressed from a bacterial source, by ion-exchange chromatography; and (c) addition of a blocking agent to the eluate of step (b).

As indicated therefore, a similar method would be used to isolate the cloned, chemically identical hementin, from micro-organisms in which the hementin has been expressed, as would be used in isolation of hementin from leech tissue or secretions.

Preferably, sodium chloride buffer is used as eluant in step (b). The blocking agent in step (c) is to prevent purified hementin losing activity on lyophilization, freezing or thawing; an example of such a blocking agent is bovine serum albumin.

Typically, the method further comprises the use of a heparin Sepharose column to eliminate contamination of the product by inhibitor Factor Xa and also gel filtration chromatography to improve the purity of the product.

There is also provided by the present invention therefore a product obtainable by the isolation method as hereinbefore described, said product being capable, when administered in a therapeutically effective amount to an animal patient (such as a human patient), of selectively dissolving or deaggregating platelet aggregates. Preferably, the product comprises hementin, which is typically essentially pure hementin.

A small scale hementin isolation and purification procedure has previously been described (Swadesh, J. K., Huang, I. Y and Budzynski, A. Z. 1990. Purification and characterisation of hementin, a fibrinogenolytic protease from the leech *Haementeria ghilianii;* J. Chromatography 502: 359–369). However, the latter procedure uses a strong anion exchange process and an ammonium bicarbonate buffer and cannot be used for large scale or pharmaceutical use for the following reasons.

(1) The ammonium bicarbonate buffer in the presence of calcium chloride results in an insoluble precipitate, presumably calcium carbonates, upon lyophilization.

(2) The purified hementin loses most of its activity upon freezing and thawing, as well as lyophilization.

(3) The procedure can result in a product contaminated with detectable amounts of inhibitor of coagulation Factor Xa, known to occur in the salivary glands of the leech *Haementeria ghilianii* (Blankenship et al. 1990; Biochem. Biophys. Res. Comm. 166: 1384–1389).

The composition comprising hementin used in the method according to the invention in addition has anticoagulant and fibrinolytic activity, which (together with the activity on platelet aggregates) act additively or synergistically on one or more steps of the process of blood coagulation. Compositions comprising hementin, alone or in combination with other anticoagulants, thrombolytic agents or anti-platelet agents, may also be used according to the invention for the prevention or therapeutic treatment of thrombosis.

A pre-requisite for platelet aggregation is the binding of fibrinogen to GpIIb-IIIa receptors on activated platelets. Activation by physiological agonists such as collagen, thrombin and ADP results in the exposure of binding sites for fibrinogen on the platelet surface resulting in the crosslinking of platelets through the Aa chains of fibrinogen bound to GpIIb-IIIa receptors on the activated platelets.

We have found that compositions comprising hementin have an effect on this process, and can not only prevent platelet aggregation but also result in platelet deaggregation.

We were able to elicit extensive deaggregation of ADP induced platelet aggregates by means of compositions comprising hementin. Extensive deaggregation occurred using ADP but less effectively when high concentrations of other inducers such as collagen were tried. This may be because when these other inducers are used, types of platelet linkage may occur other than those utilising fibrinogen.

The ability of compositions comprising hementin to selectively deaggregate platelets is a property not shared by plasminogen activators such as TPA or streptokinase. This gives compositions comprising hementin a possible advantage in that they may have selectivity for platelet-rich thrombi which are refractory to such plasminogen activators. Therefore, because thrombi are complex multicomponent structures of varying ages and composition, and anti-platelet therapy is likely to become a significant therapeutic strategy, the identification of the platelet directed mode of action of hementin is important progress towards providing new tools for the treatment of thrombotic disease.

According to a further aspect of the invention, therefore, there is provided a composition comprising hementin, for use in the manufacture of a medicament for the therapeutic deaggregation of platelet aggregates and optionally also for the inhibition or prevention of platelet aggregation.

There is also provided a composition comprising a material capable of selectively cleaving between D and E domains of the fibrinogen linkages present in said platelet aggregates, for use in the manufacture of a medicament for the therapeutic deaggregation of platelet aggregates and optionally also for the inhibition or prevention of platelet aggregation.

The present invention further comprises the use of compositions comprising hementin for the preparation of medicaments for administration to a patient together with a plasminogen activator, such as TPA, for clot lysis. Such administration may be without any further inhibitor of platelet aggregation.

The present invention still further comprises the use of compositions comprising hementin together with hirudin or other leech derived anti-coagulant (such as that disclosed in our prior PCT Patent Specification WO90/05143).

The present invention therefore further comprises a pharmaceutical formulation for the treatment of platelet aggregates, which comprises hementin, an inert carrier or excipient therefor, and, optionally, one or more further active materials, such as a leech-derived anti-coagulant. Such an anticoagulant is preferably an anti-thrombin, which is typically a hirudin or hirudin analogue, or Factor Xa.

The carrier or excipient is preferably such that the formulation can be administered intravenously; an example of a suitable carrier is sterile saline. The intravenous formulation typically contains sufficient hementin that, when administered to a patient, the latter has 20 to 100 units of hementin per ml of blood.

We have established that compositions comprising hementin have four anti-coagulant and anti-thrombotic properties which are effective by themselves or in combination with other drugs directed at similar targets. These properties may be summarised as:

1. Anti-coagulant—inhibition of the ability of blood to clot (in the case of purified hementin, this is believed to result from fibrinogenolytic activity which depletes fibrinogen available for clotting).
2. Fibrinolytic—an ability to dissolve fibrin clots.
3. Inhibitor of platelet aggregation—an ability to prevent aggregation initiated by a number of agonists via action on fibrinogen.
4. Platelet deaggregation—a unique and surprising ability to selectively deaggregate pre-formed platelet aggregates.

The present invention will now be described in more detail, with reference to the following examples, in which references to crude hementin relate to compositions having an activity of approximately 100 (typically 25–100) u/mg protein, while references to purified hementin relate to compositions having an activity greater than 1000 u/mg protein.

The unit activity of hementin is defined as the number of micrograms per milliliter of fibrinogen rendered incoagulable by thrombin per minute at 37 degrees Celsius.

The present invention also provides new more sensitive assays for detecting and measuring this hementin activity. We have discovered that hementin is very salt dependent and consequently activity must be measured at near physiological levels of NaCl in the reaction buffer. Our reaction conditions were: 50 mM Hepes, 10 mM $CaCl_2$, 0.15 mM NaCl, 0.1% Brij 35, pH 7.5. In contrast, in the paper mentioned above by Swadesh et al the assay buffer was 150 mM Hepes, pH 7.9 and 10 mM $CaCl_2$. In addition we also provide a sensitive assay based on analysis of fibrinogen breakdown products detected by HPLC.

There is further shown by the examples isolation and purification techniques for hementin and subsequent characterisation of its chemical and physical properties.

EXAMPLE 1

Purification of Hementin from the Anterior Salivary Gland

The anterior glands of 117 hungry third fed *Haementeria ghilianii* were manually dissected and frozen on dry ice. The glands were crushed to a fine powder in dry ice and then homogenised and thawed in 20 mM Hepes, 10 mM $CaCl_2$, pH 7.5. The homogenate was centrifuged (1000×g) to remove insoluble cell debris and then further centrifuged (10000×g) and filtered (0.45 micron Filter). This material was the starting point for purification and was designated Stage I material.

Hementin was then purified by high performance anion-exchange chromatography. Stage I material was brought up to 10 ml in Hepes buffer described above and 1–2 ml added at a time to a DEAE-5PW column (1×5 cm; Waters-Millipore). The activity eluted between 80–150 mM NaCl using a linear salt gradient.

To the pooled active fractions was added 1 mg/ml bovine serum albumin ('Cohn Fraction 5', Sigma) before lyophilization or freezing. The results of a typical purification are as follows:

|          | Specific Activity (Units/mg) | Total (Units) | Recovery % |
|----------|------------------------------|---------------|------------|
| Stage I  | 292                          | 16,600        | —          |
| Stage II | 600                          | 13,200        | 83         |

EXAMPLE 2

Gel Filtration Purification of Anterior Salivary Gland Material

Post anion-exchange material (Stage II) was pooled as described in Example 1. The pool was applied to a molecular sieving column (Superdex 200; Pharmacia) using a buffer containing 20 mM Hepes, 10 mM $CaCl_2$, pH 7.5. The fractions containing activity were pooled. To the pool was added 1 mg/ml bovine serum albumin (BSA) prior to freezing or lyophilization. The pool was then freeze-dried and designated Stage III material. The results of a typical purification are as follows:

|           | Specific Activity (Units/mg) | Total (Units) | Recovery % |
|-----------|------------------------------|---------------|------------|
| Stage III | 1400                         | 5,600         | 35         |

EXAMPLE 3

Purification of Hementin from the Posterior Salivary Gland

Figure 2:
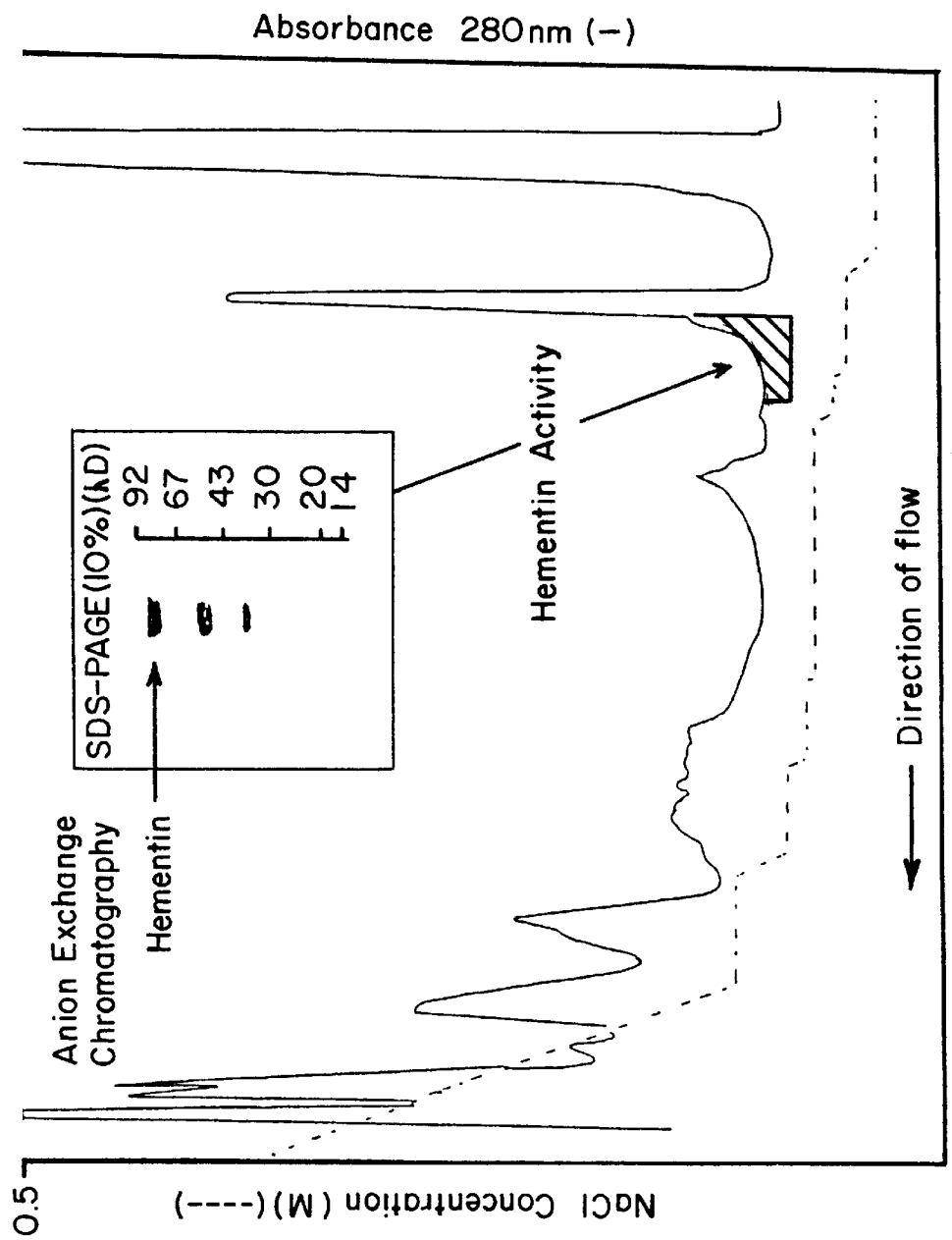
FIG. 2 shows an elution profile of hementin when subjected to high-performance anion exchange chromatography on a DEAE-5PW column. The inset shows a reducing SDS-PAGE profile of a typical hementin-containing fraction.

The posterior glands of 118 hungry fed *Haementeria ghilianii* were manually dissected and frozen on dry ice. Stage I and Stage II (post ion-exchange) material were prepared as in Example 1. During elution of the Stage II material from the anion-exchange column, aliquots of fractions containing activity were analysed by SDS-PAGE (10%) gels under reducing conditions (FIG. 2 insert). To the active pool was added 1 mg/ml BSA prior to freezing or lyophilization.

The results of a typical purification were as follows:

|          | Specific Activity (Units/mg) | Total (Units) | Recovery % |
|----------|------------------------------|---------------|------------|
| Stage I  | 1,827                        | 40,929        | —          |
| Stage II | 11,506                       | 28,650        | 70         |

EXAMPLE 4

Purification of Anterior Salivary Hementin by HPLC

Figure 3:
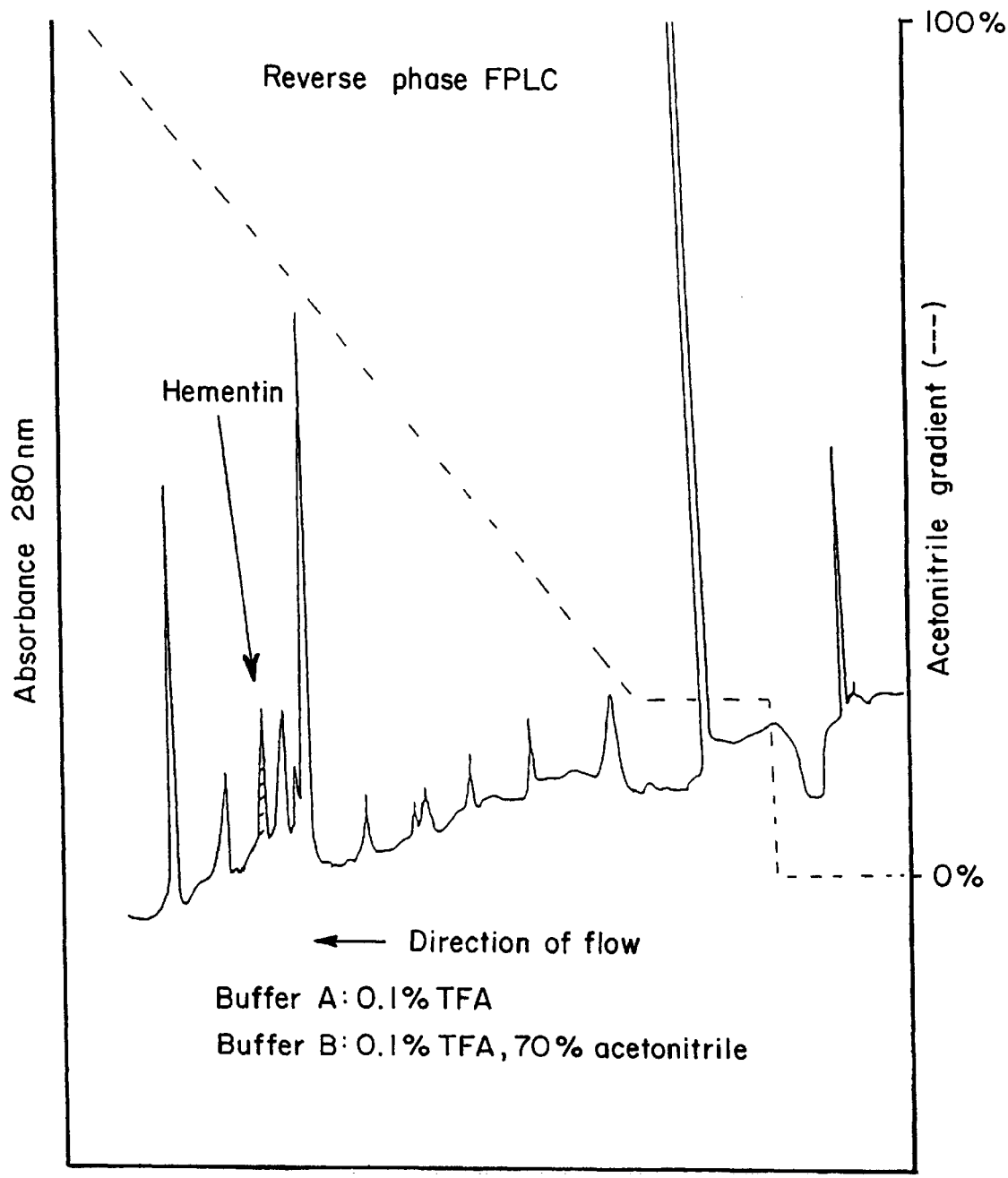
FIG. 3 shows the purification of hementin by reverse-phase high-performance liquid chromatography, using an elution gradient of acetonitrile in trifluoroacetic acid.

The anterior glands of 55 starved third fed *Haementeria ghilianii* were manually dissected and frozen on dry ice. The glands were homogenised in 10 ml of 20 mM Hepes, 10 mM $CaCl_2$, pH 7.5 using acid-washed sand. The homogenate was centrifuged (10,000×g) and the supernatant passed through a 0.43 micron filter. This was loaded onto an anion exchange column (DEAE-5P, Waters) and eluted using a salt gradient. Fractions were collected and assayed for activity and for protein (280 nM). Activity was found in fractions 21–25 and in 29/30. Fractions 21 and 23–25 were pooled and used for further purification by reversed phase hydrophobic interaction chromatography (RP-HPLC). SDS-PAGE gels were run on fractions containing activity. The pooled active fractions from the anion exchange run were applied to a RP-HPLC column (C18, Waters) in 0.1% trifluoroacetic acid (TFA) and eluted with a gradient of 70% aqueous acetonitrile, 0.1% TFA (FIG. 3). Fractions were collected and found to contain activity in fractions 53–55 which were freeze dried. The protein content was approximately 40 ug SDS-PAGE analysis of the product under reducing conditions gave a molecular weight of about 80,000 which corresponds to that of hementin. Activity against fibrinogen was detected using SDS-PAGE analysis of fibrinogen fragments following incubation with hementin-containing fractions.

EXAMPLE 5

Isoelectric Focussing of Hementin

Knowledge of the precise isoelectric point (pI) value of proteins is useful in maximising the conditions for purification. In order to determine this characteristic property for hementin, the following experiment was conducted. The active fraction following application onto anion-exchange chromatography, as indicated in FIG. 2, was further purified by FPLC on a Superose 12 gel filtration column, pre-equilibrated in 20 mM Hepes buffer, pH 7.5 containing 0.2 M NaCl, 10 mM $CaCl_2$ and 0.1% Tween 80. 200 ul of the sample was loaded onto the column and eluted with the above buffer at 0.4 ml/min. The effluent was collected in fractions and its absorbance was monitored at 280 nm. Two major protein peaks eluted at about 30 min and 40 min, respectively. Based on a fibrinogenolysis assay (as described in Example 12, below), the hementin peak was determined to be the one eluting at about 30 min.

This peak was concentrated and desalted on Sephadex G-25. After further concentration, an aliquot of the sample was analysed for its isoelectric point (pI) on a PhastGel 3-9 using a Pharmacia Phast System. The sample was applied centrally onto the gel. After staining with Coomassie Blue, one major band at approximately pI of 6.25±0.1 was thought to correspond to hementin. Trace amounts of impurities could also be visualised on the gel at pI values below 4.6. Based on intensity of the stain, it is assumed that these impurities account for less than 5%. The pI of hementin is therefore approximately 6.25±0.1.

EXAMPLE 6

Fibrinogenolysis Assay

Figure 4:
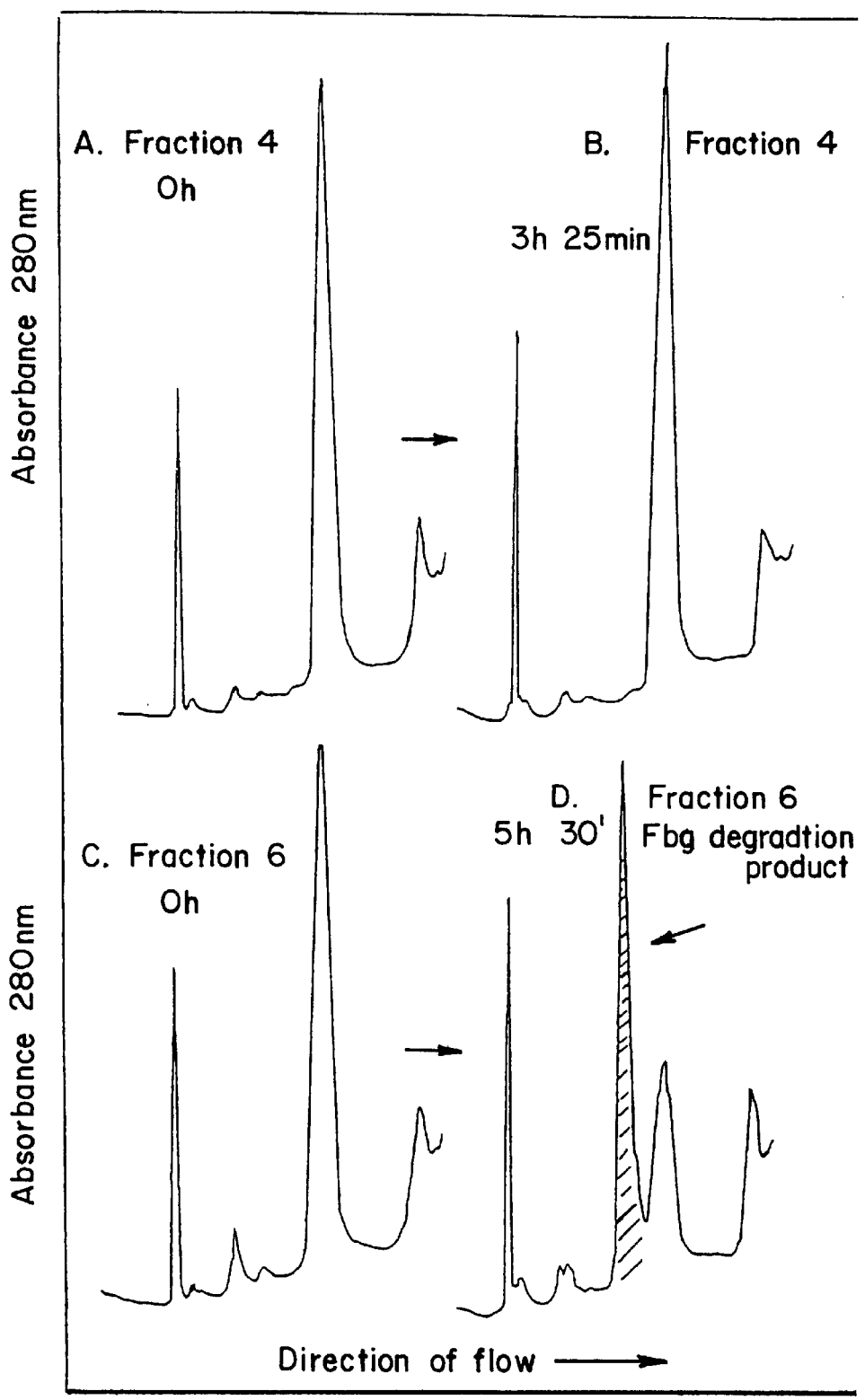
FIGS. 4A–4D show a fibrinogenolysis assay, in which fibrinogen breakdown products are detected by high-performance liquid chromatography on an RP300-C8 column.

In order to recognise peaks of activity involving very limited amounts of material it was necessary to develop the following new, fast, convenient and very sensitive assay for fibrinogenolysis. The assay involves incubation of enzyme or purified column fractions with fibrinogen followed by rapid analysis of fibrinogen breakdown products on HPLC (RP300-C8). Stage II enzyme (50 microliters) or column fractions were incubated in a Reacti-Vial with 50 microliters of 50 mM HEPES buffer, pH 7.5, 2 mM $CaCl_2$, 50 microliters of 0.15 mM NaCl and 50 microliters of fibrinogen (5 mg/ml). Of this mixture (20 microliters) was diluted with 30 microliters 20 mM HEPES buffer and the total volume was immediately injected onto an ABI 130A analytical chromatograph with an RP30-CB column to produce a zero time chromatogram. The reaction mixture was eluted with a gradient between 0.1% TFA in water (solvent A) and 0.1% TFA in 80% aqueous acetonitrile (solvent B). The column was equilibrated at 35% B followed by a 5 minute rise to 45% B and a 20 minute gradient 50–55% B. The rest of the vial was incubated at 37 degrees Celsius for a desired period, such as half an hour, which was sufficient to detect activity in the form of changed HPLC elution profile due to the presence of fibrinogen degradation product (FIG. 4). Fibrinogen alone eluted as a single peak from the HPLC column at 52% of solvent B. After 30 minutes incubation at 37 degrees Celsius with hementin the fibrinogen peak had been converted (90%) to an earlier elution peak peak (50%B) and one that appeared to elute later (53%B) than the original fibrinogen.

Inactive materials did not change the elution pattern for as much as 24 hours.

EXAMPLE 7

Purification of Anterior Gland Hementin by HPLC

Figure 5A:
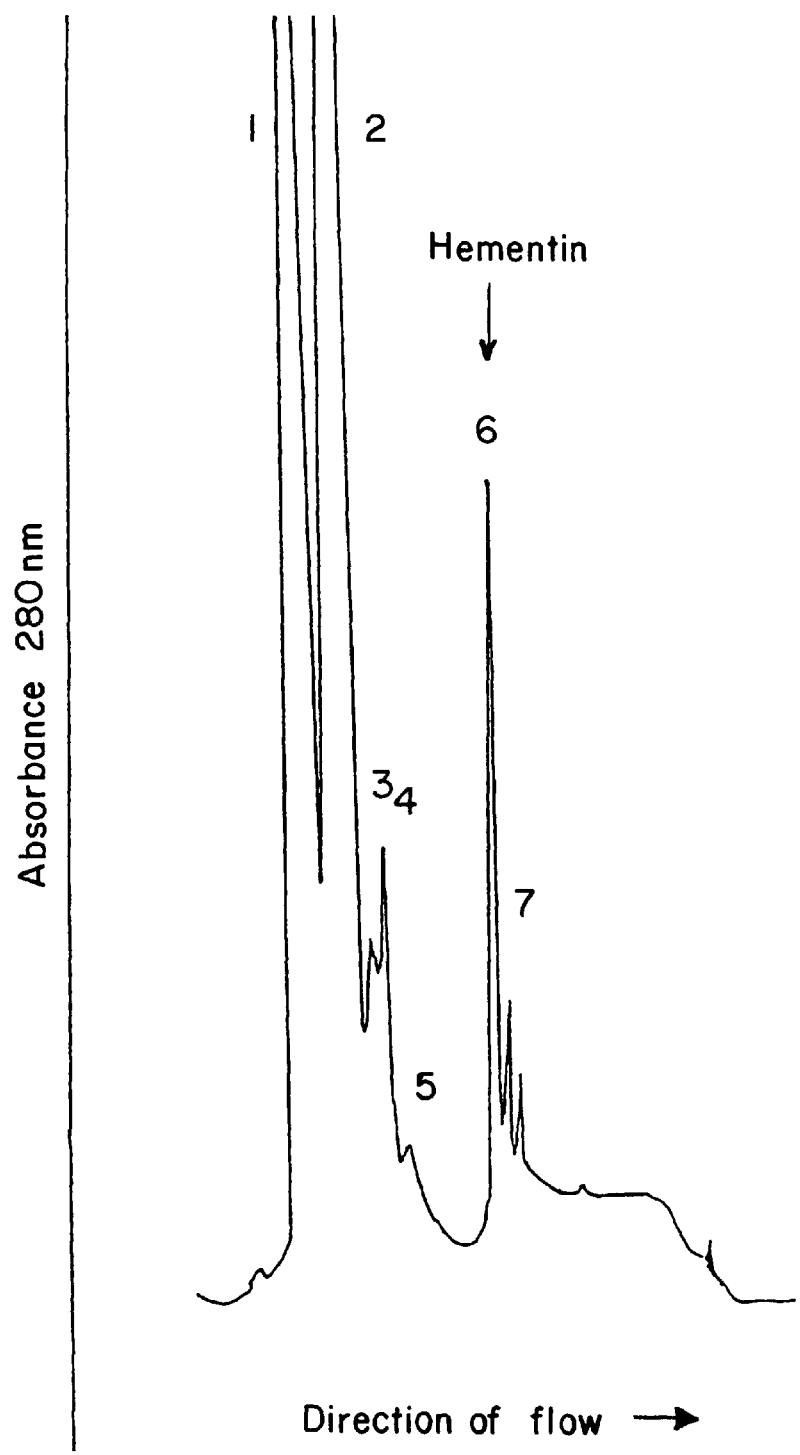
FIG. 5A shows the further purification of hementin by high-performance liquid chromatography on an RP300-C8 column.

Stage II material, such as that described in Example 1, was purified by HPLC on a RP300 (C8) column. Solvent A was 0.1% TFA in water, Solvent B was 0.1% TFA, 80% aqueous acetonitrile. The gradient was 25 to 65% Solvent B in 30 min. Upon elution the material separated into 7 fractions as shown in the elution profile (FIG. 5A). Under the assay conditions fractions 6 and 7 showed activity, as determined by the sensitive assay described in Example 6, whereas all other fractions were inactive. Fraction 6 contained the major activity.

EXAMPLE 8

Amino Acid Composition of Anterior Gland Hementin

Amino acid analyses were performed after 24 hour vapour phase HCl hydrolysis and modification with phenyl isosolcyocyanate (PITC).

Figure 5B:
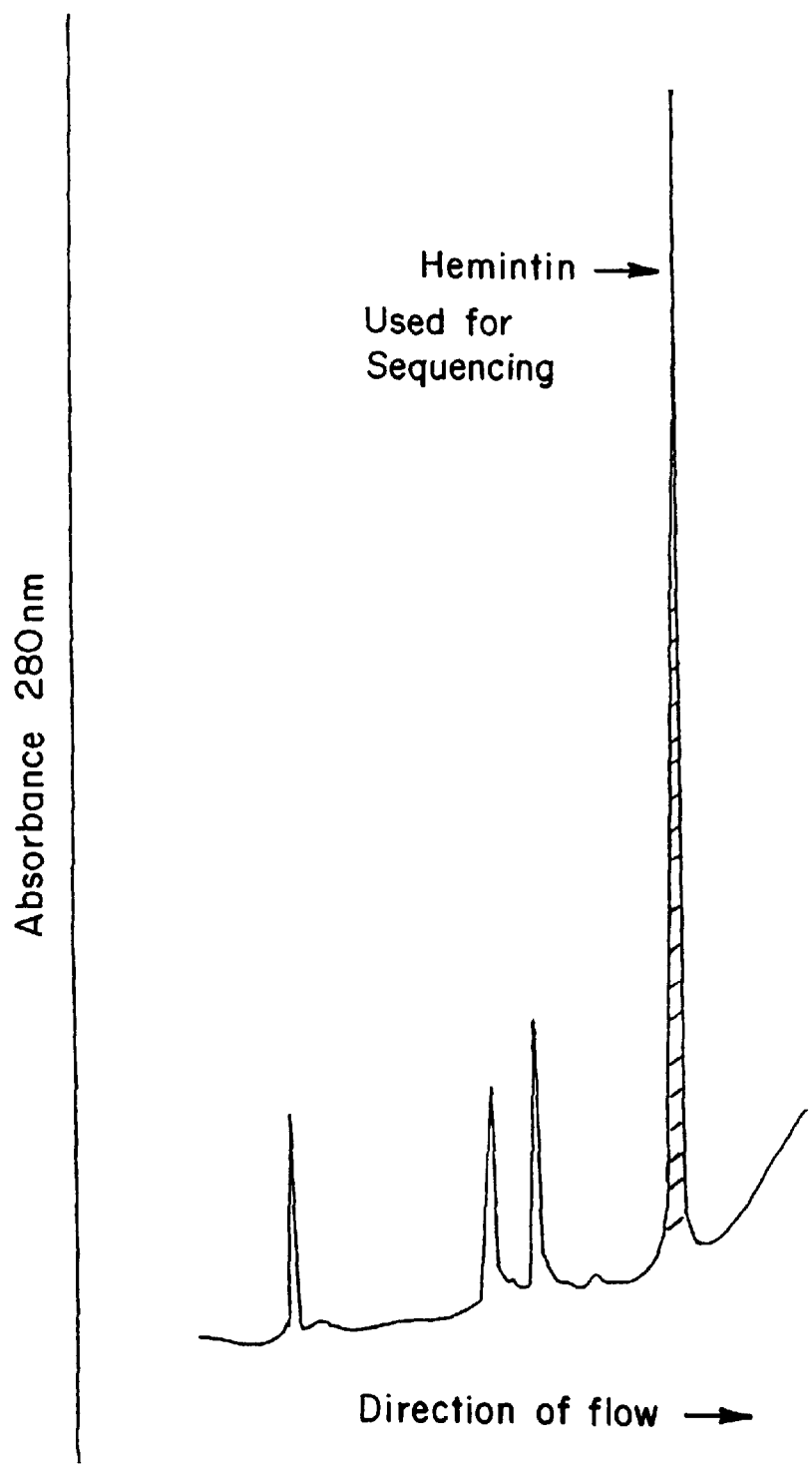
FIG. 5B shows the rechromatography of fraction 6 derived from the experiment shown in FIG. 5A.

Pooled Peak 6 (as shown by peak 1 in FIG. 5B), prepared as described in Example 7, was put onto a Waters 840 amino acid analysis system (Picotag). Multiple regression analysis gave a minimum molecular weight of 83,000 as the best fit factor for all amino acid values, calculated by a computer programme of Black and Hogness. The amino acid composition of anterior gland hementin was determined to be as follows:

| | |
|---|---|
| asp ⎫ | |
| asn ⎭ | 87.89 |
| thr | 31.89 |
| ser | 78.94 |
| glu ⎫ | |
| gln ⎭ | 80.79 |
| pro | 7.99 |
| gly | 100.32 |
| ala | 42.02 |
| ½cys | 25.08 |
| val | 31.07 |
| met | 27.23 |

-continued

| | |
|---|---|
| ile | 30.04 |
| leu | 59.70 |
| tyr | 29.15 |
| phe | 28.85 |
| his | 26.93 |
| lys | 42.24 |
| trp | — |
| arg | 34.40 |

EXAMPLE 9

N-terminal Amino Acid Sequence of Anterior Gland Hementin

In preparation for amino acid sequence analysis, Peak 6 hementin, prepared as per Example 7, was collected manually in dichlorodimethylsilane-treated glass tubes. The gradient was run at 100 microliters/min and Peak 6 was collected in less than 200 microliters in one tube. The pooled Peak 6 hementin was immediately concentrated to less than 100 microliters and then transferred in 20 microliters portions to a polybrene-treated membrane of an Applied Biosystems 477A pulse-liquid phase protein sequencer. For sequence analysis the fractions were collected without Hepes buffer. The N-terminal sequence was determined to be as follows:

```
1                      5
thr-thr-leu-thr-glu-pro-glu-pro-pro-(or phe or 10
asn)-leu-thr-thr(or phe)-leu-thr(or 15                              20
asn)-phe-val-arg(or asp)-ile(or asn)-val-asn(or 25
lys)-val(or leu)-glu(or asp)-met-pro-ile-phe-val(or 30
asp or gly or ala or phe)-met-ala-thr(or 35
arg)-ala-asn(or gln)-ser-gln-ile-thr(or tyr)-ser(or 39
thr or tyr)-thr(or lys)-phe-
```

EXAMPLE 10

Internal Amino Acid Sequence of Anterior Gland Hementin

Pooled Peak 6 hementin, prepared as per Example 7, upon trifluoroacetic acid hydrolysis yielded a peptide fragment with the following sequence:

```
 1             5              10            15
 *  *  *  *  *          *  *
gly-tyr-thr-asn-tyr-ala-lys-phe-leu-asp-tyr-leu-pro-val-glu-arg- 20
gly-ile-pro-leu
```

Portions of this sequence in positions 2–6 and 8–9 (indicated by asterisks), respectively, correspond to the sequence reported by Swadesh et al (1990. J. chromatography 502: pp. 359–369) and designated a contaminating peptide in hementin purification. Their sequence was:

glu-val-tyr-thr-asn-tyr-ala-ser-phe-leu-

Our sequence probably does not correspond to a contaminating peptide, but to result from acid hydrolysis of an asn-gly bond within the hementin molecule.

EXAMPLE 11

Amino Acid Sequence of Posterior Gland Hementin

Figure 6:
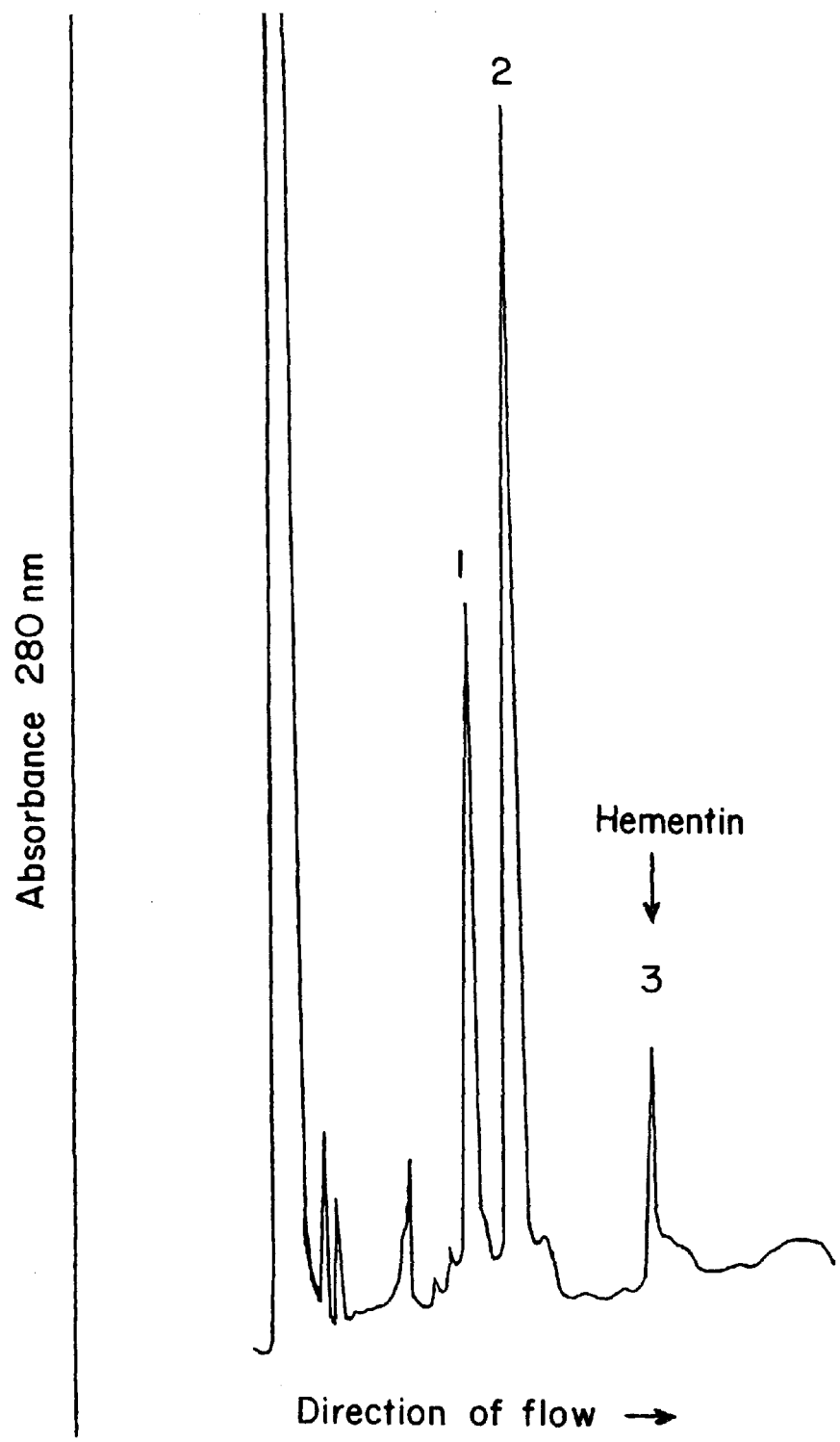
FIG. 6 shows the final step of purification of hementin prepared from posterior glands, using an RP300-C8 column.

Stage II hementin prepared from the posterior glands as described in Example 3 were purified by HPLC as described in Example 7. The protein profile was different from that prepared from anterior gland Stage II hementin, with three major peaks (FIG. 6). Activity was found in Peak 3. Pool fractions corresponding to the active peak (Peak 3) were put onto a pulse-liquid phase protein sequencer Applied Biosystems 477A. The N-terminal sequence was determined to be as follows:

```
 1             5              10            15
thr-thr-leu-thr-glu-pro-glu-pro-phe-leu-thr-tyr-leu-thr-phe-val- 20
arg(or lys)-ile-val-asn(or lys)-val(or leu)-glu-met-pro-ile-phe- 30              35           39
val-met-ala-thr-ala-asn-ser-gln-ile-thr-ser-thr-phe-
```

EXAMPLE 12

Anti-Coagulant Effect

The plasma anti-coagulation rate by crude hementin at a dose of 30 u/ml (units/ml) was followed by measuring the prothrombin time (PT) using the Manchester reagent (Thrombosis Research Foundation, Stockport, UK); activated partial thromboplastin time (APTT) with kaolin/Bell and Alton platelet substitute (Diagnostic Reagents, Thame, UK); thrombin clotting time (TCT) with bovine thrombin (Baxter Healthcare, Newbury, Berks) and atroxin clotting time—a purified extract of Bothrops atrox venom (Sigma) used at a concentration of 0.5 mg/ml. The PT, TCT, and APTT were measured in citrated plasma.

The results of these studies with crude hementin were as follows:

| Test | Time to incoagulate PRP (min) | control clotting time |
|---|---|---|
| PT | <1.0 | 15 sec. |
| APTT | <1.0 | 40 sec. |
| TCT | <2.5 | 15 sec. |
| Atroxin | 15–20 | 17 sec. |

This shows the rapid effect of crude hementin on the coagulability of plasma.

The results with purified hementin on the coagulation of citrated plasma at 70 u/ml were as follows:

|  | PT | atroxin | TCT | APTT |
|---|---|---|---|---|
| CONTROL | 19 | 25 | 15 | 55 |
| 5 min | 18 | 26 | 15 | 54 |
| 10 min | 20 | 26 | 15 | 53 |
| 20 min | >300 | 60 | >300 | >300 |
| 30 min | — | >300 | — | — |

Figure 7:
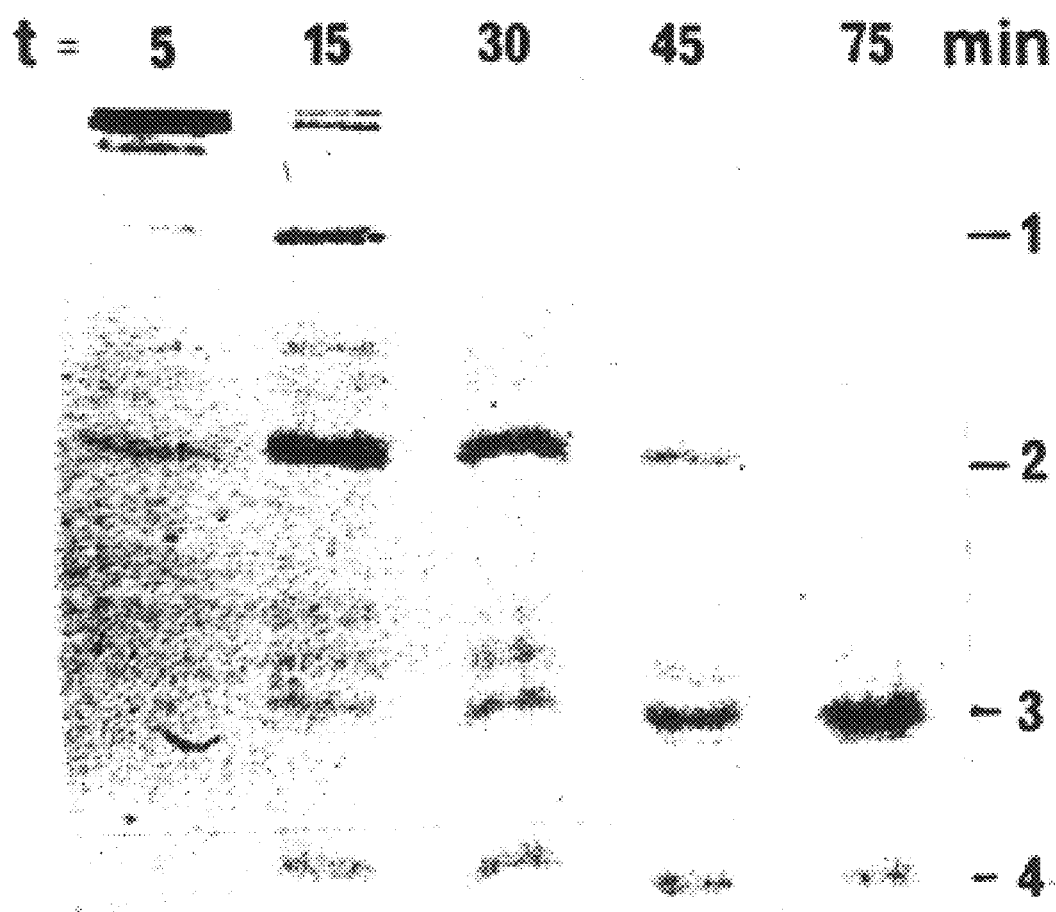
FIG. 7 shows an SDS-PAGE profile of fibrinogen degradation products generated by the action of hementin.

The effect of purified hementin on fibrinogen is shown in FIG. 7, which shows the results of SDS-polyacrylamide gel electrophoresis, giving the times of generation of fibrinogen fragments and their molecular size. Fibrinogen (0.5 mg/ml) was incubated with purified hementin (160 u/ml) at 37 degrees Celsius and aliquots taken at timed intervals for analysis by SDS-PAGE under non-reducing conditions. Fibrinogen major fragments (1–4) corresponding to Fragments 4 (MW 225 kdaltons); 6 (MW 157 kdaltons); 7 (MW=133 kdaltons); and 8 (MW=100 kdaltons) described by Malinconico were detected.

EXAMPLE 13

Measurement of Platelet Aggregation

Crude hementin was extracted from the anterior glands of *Haementeria ghilianii*. The lyophilized crude hementin was reconstituted with isotonic saline prior to use for platelet studies or in 50 mM Hepes, 10 mM $CaCl_2$, 0.1% Brij 35, pH 7.5 for in vitro assay.

Freshly obtained blood samples were collected by venepuncture from the antecubital vein of 5 healthy human volunteers who had received no medication nor alcohol for at least two weeks. Paired samples from each volunteer were immediately placed in siliconised vessels containing two different anticoagulants—1:9 v/v 0.105 M sodium citrate or heparin (at a concentration which did not result in spontaneous platelet clumping—20 IU/ml blood). Samples were centrifuged at 200 g for 10 min and harvests of platelet rich plasma (PRP) 9 were prepared to contain 250–350×10 per liter of platelets.

Where necessary, PRP was diluted with autologous platelet poor plasma (PPP). All test procedures were performed within the second hour following venesection. Platelet aggregation and deaggregation studies were performed in a four channel aggregometer at 37 degrees Celsius. Acid soluble Type I collagen (Chronolog Corp., Havertown, Pa.), ADP (Sigma Chemical Co, Poole, Dorset) and, in the case of citrated samples—bovine thrombin (Baxter Healthcare Ltd., Newbury, Berks), were used to induce platelet aggregation. The effect of pre-incubating (5 min) PRP (dilution 1:9) with hementin before the addition of inducer was determined. Platelet deaggregation by purified hementin was determined upon its addition to the PRP/inducer mixture when a threshold level of aggregation was reached. Appropriate controls using isotonic phosphate-buffered saline instead of purified hementin were performed with each inducer.

Platelet Aggregation in PRP Pre-Incubated with Hementin

Figure 8A:
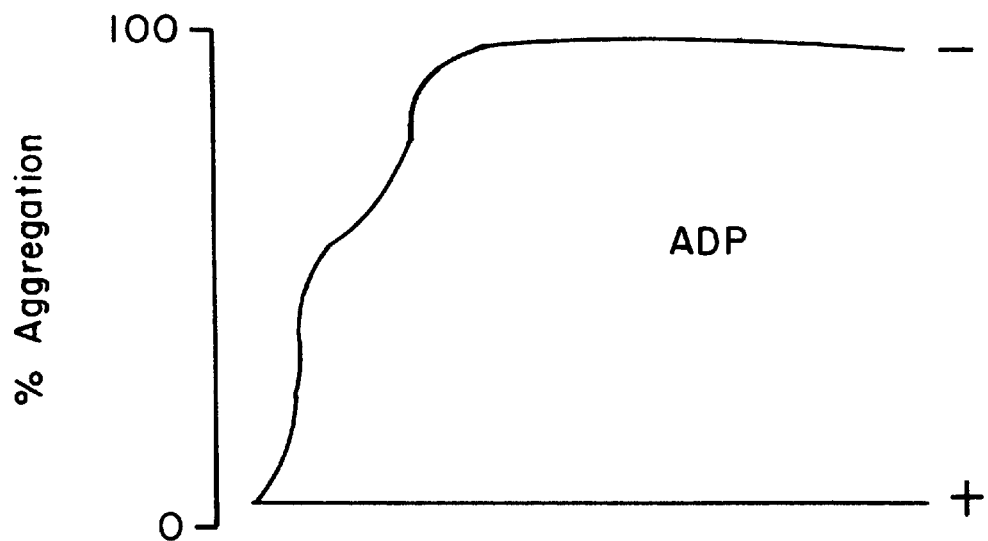
FIGS. 8A–8C show the platelet aggregation of platelet-rich plasma induced by ADP, collagen, and thrombin, when pre-incubated with hementin.

The loss of fibrinogen coagulability by thrombin in PRP pre-incubated with purified hementin, was associated with significant reduction in platelet aggregation responses in both citrated, hirudinised and heparinised blood. Typical responses, which were similar in all five volunteers are shown in FIG. 8. Platelet aggregation with 1.0 ug/ml of thrombin as inducer was completely absent in heparinised PRP (FIG. 8c). When citrated plasma was used, the response with 1.0 ug/ml thrombin was reduced to less than 40% of that of the control, with rapid deaggregation and complete loss of subsequent plasma coagulability.

Figure 8B:
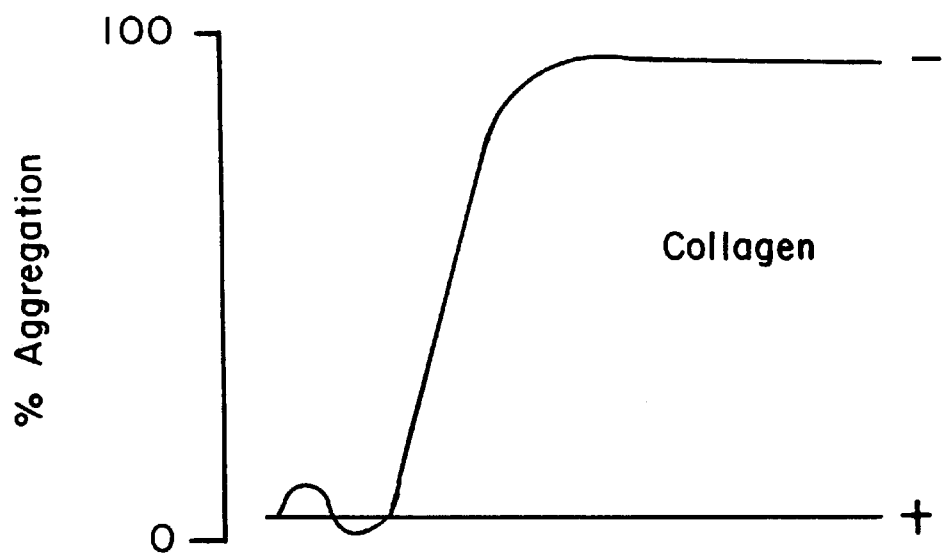
Figure 8C:
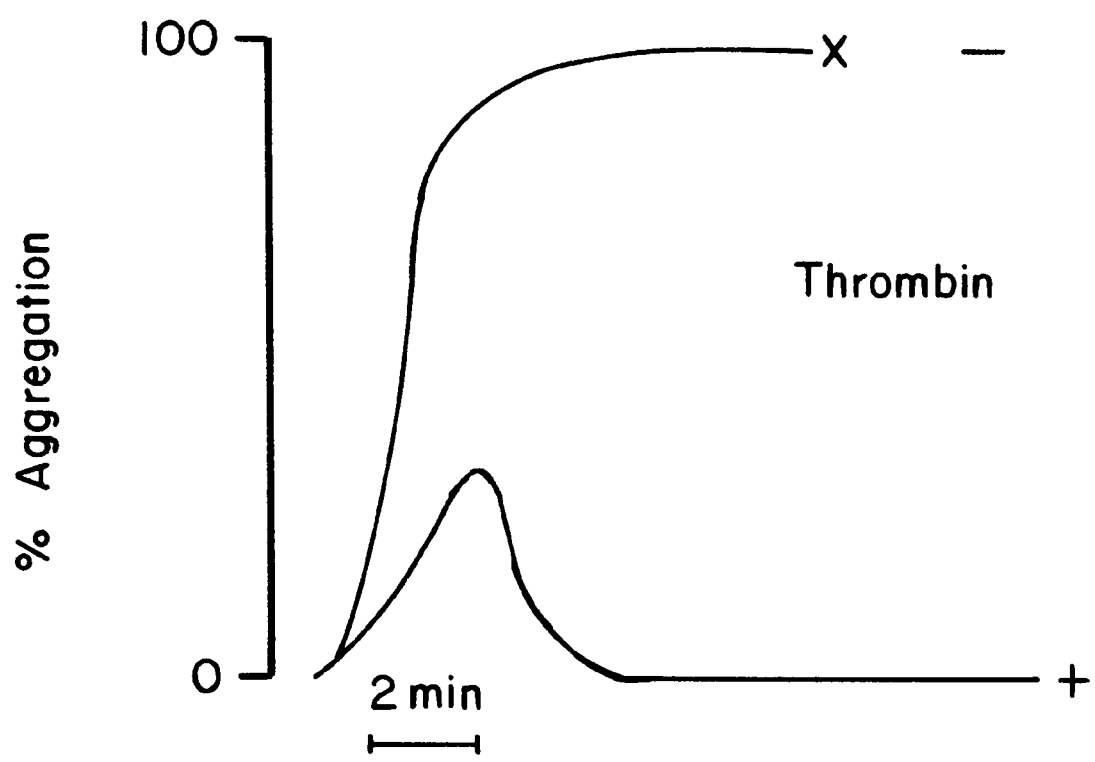

Platelet aggregation responses with collagen (2 ug) were almost completely abolished in both citrated and heparinised plasma (FIG. 8b).

Typical aggregation responses with a low concentration of ADP (0.5 uM) were similar in citrated and heparinised samples. However, with higher concentrations of ADP (2.5 uM), responses in heparinised plasma were different to those in citrate. Whereas platelet aggregation in citrated samples was not affected by hementin at this dose, aggregation responses in heparinised samples were markedly reduced to less than 50% of controls (FIG. 8a). The apparent loss of potency of hementin in citrated plasma may be because hementin activity is somewhat inhibited in the presence of citrate.

EXAMPLE 14

Platelet Deaggregation by Hementin

Platelet deaggregation resulting from the addition of hementin to plasma containing aggregated platelets is shown in FIG. 9. Platelets in normal human PRP were activated and induced to aggregate through the action of ADP, collagen or thrombin agonists. Hementin was added to these aggregates and the time course and extent of any effect followed in the platelet aggregometer (FIG. 9). In citrated or hirudinised plasma ADP at a dose of 1 to 5 uM induced a characteristic (biphasic in the case of citrated plasma) platelet aggregation curve and this was maintained over at least a ten minute period. Addition of hementin (in the concentration range 10 to 100 u/ml) to citrated (FIG. 9a) or hirudinised (FIG. 9b) ADP-induced platelet aggregates caused rapid and irreversible deaggregation of platelets (FIG. 9a,b). In heparinised plasma, a similar observation of deaggregation was made (data not shown). Platelet preparations deaggregated with hementin showed no evidence of change in size distribution compared to unaggregated controls.

Once deaggregation by hementin in hirudinised PRP had taken place, reaggregation by further addition of either ADP (10 uM) or collagen (5 ug/ml) was not significantly induced (FIG. 9b), probably because of fibrinogen depletion within the plasma and/or time necessary for full recovery of platelet function.

In citrated, hirudinised or heparinised PRP, collagen (2 ug/ml) induced a characteristic aggregation response. However, hementin (10–100 u/ml), at a dose range effective for ADP induced platelet aggregation (1 to 5 uM), did not cause deaggregation (FIG. 9c) in vitro. Higher doses of hementin did deaggregate collagen associated platelet aggregates in vivo.

In citrated plasma, thrombin at a dose of 0.2 ug/ml induced a transient aggregation response in PRP. At a higher agonist concentration of 1 ug/ml, a full aggregation response was obtained with subsequent clotting. Hementin significantly accelerated the spontaneous deaggregation of platelet aggregates following the sub-optimal thrombin dose of 0.2 ug/ml but did not deaggregate platelets aggregated with the higher 1 ug/ml thrombin dose, despite complete prevention of the clot formation in the controls (data not shown). The partial effect of hementin on deaggregation in citrated plasma may be due to some inhibition of hementin by citrate.

EXAMPLE 15

Effect of TPA on Platelet Deaggregation

Figure 9A:
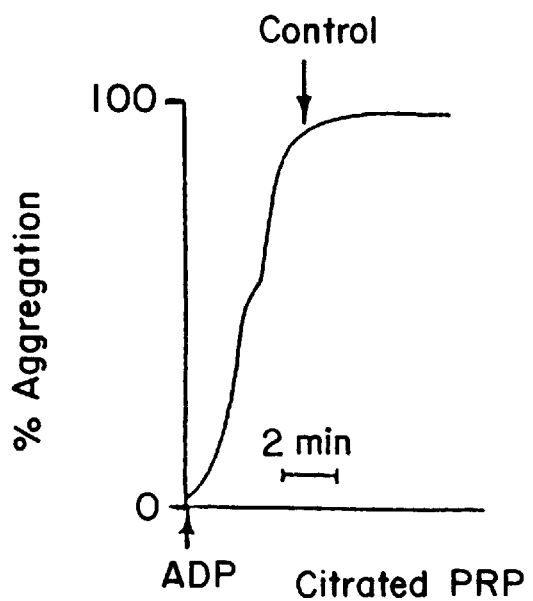
FIGS. 9A–9C show platelet deaggregation resulting from the addition of hementin to plasma containing aggregated platelets.
Figure 9B:
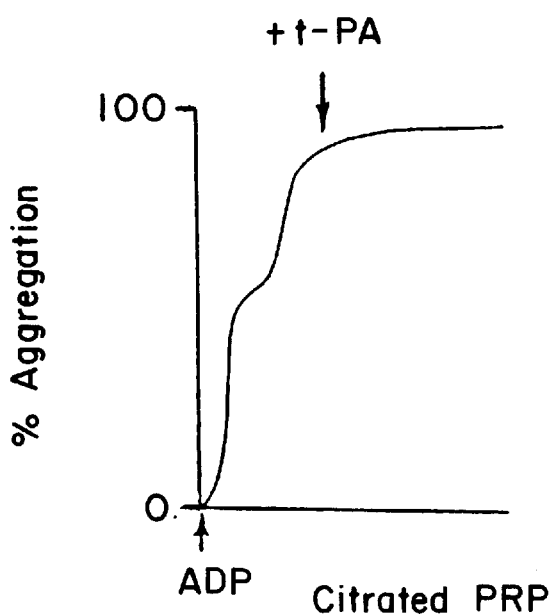
Figure 9C:
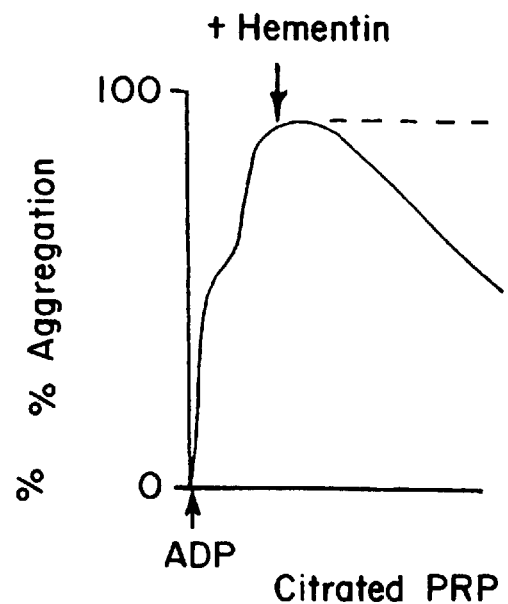
Figure 9D:
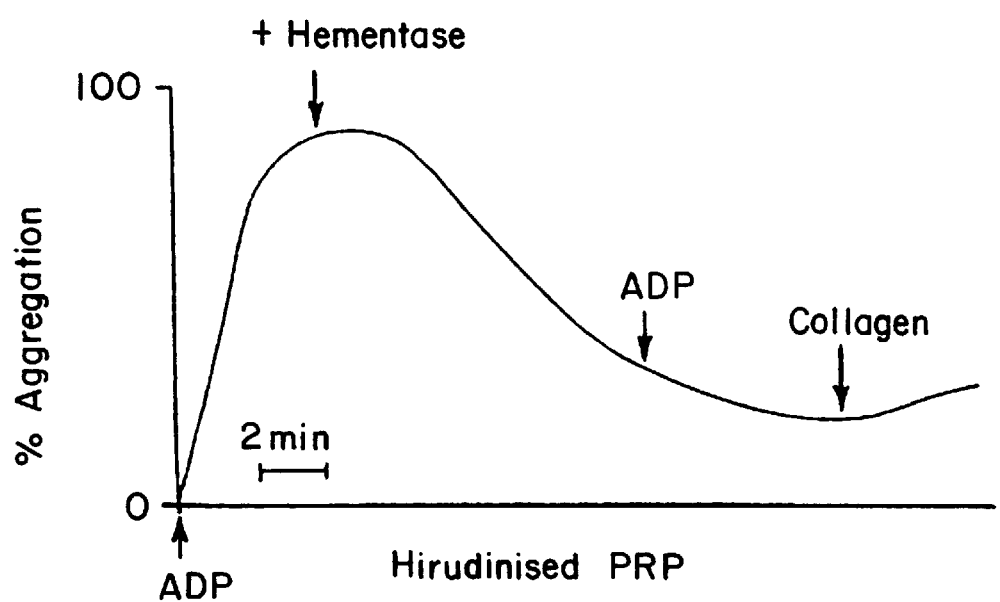
Figure 9E:
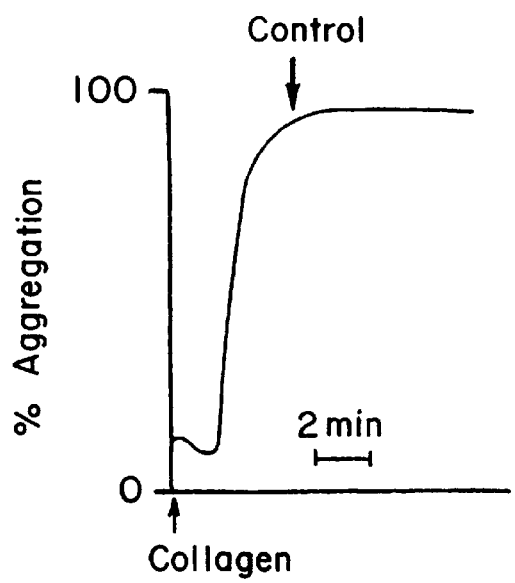
Figure 9F:
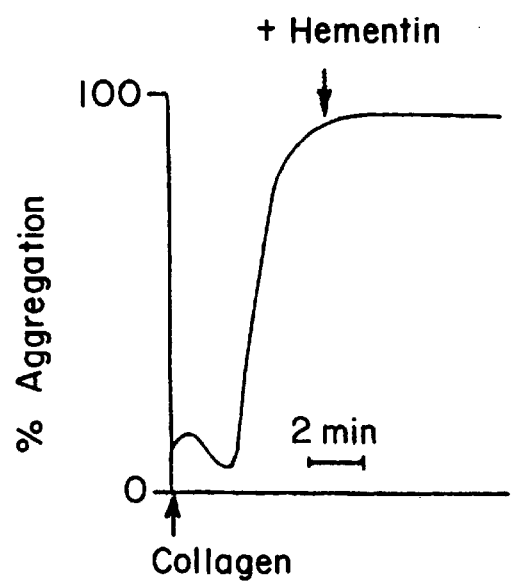
Figure 10:
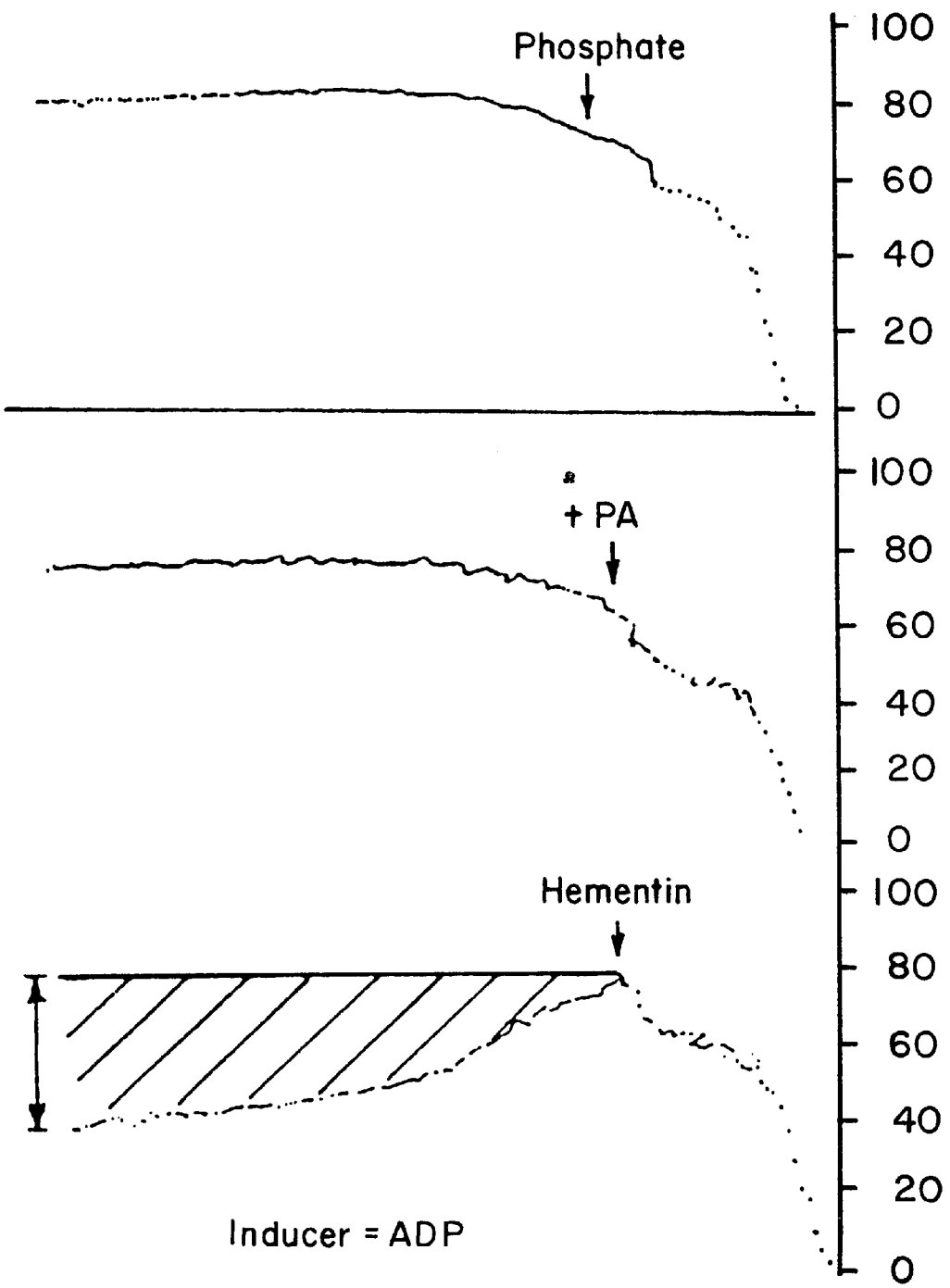
FIG. 10 compares the effect on platelet deaggregation of tissue plasminogen activator (tPA) and hementin.

To contrast the effects of hementin on platelet deaggregation with those of another thrombolytic agent, we also found, in a side by side comparison with the same PRP, that TPA at a dose up to 104 IU/ml (sufficient to cause plasma clot lysis within 2 minutes) did not cause platelets to deaggregate in citrated PRP (FIGS. 9a, 10). Human platelets were induced to aggregate using ADP (1 to 5 uM) as agonist and TPA (104 IU/ml) or hementin (20 to 70 u/ml) were added and the course of deaggregation followed in the platelet aggregometer. This clearly demonstrated that hementin has a mechanism of action different from TPA and that hementin has an added anti-platelet activity which should help in the dissolution of thrombi containing platelets, and other platelet aggregates.

EXAMPLE 16

Enhancement of Hementin Activity in Whole Blood

It is known that hementin is not inhibited by the blood's naturally occurring inhibitors of coagulation proteases (U.S. Pat. No. 4,390,630). We have made the additional significant discovery that the activity of purified hementin is greatly enhanced in whole blood. This finding is surprising and is in marked contrast to the action of TPA which is well known to be inhibited by PA-1 (plasminogen activator inhibitor-1). PA-1 has been implicated as the cause of reduced fibrinolytic capacity of plasma from survivors of myocardial infarctions (Madison, E. E. et al. 1989. Nature 339: 721–724).

By way of illustration, the following experiment was conducted to determine the relative activity of purified hementin in whole blood, plasma (from the same individual) and fibrinogen in buffer. Whole human blood was obtained by venepuncture and anticoagulated with 1:9 v/v 0.1205 M sodium citrate. An aliquot of the blood was used to obtain PRP by centrifugation at 3000 rpm for 10 min at room temperature. The reaction buffer used for purified bovine fibrinogen was: 20 mM Hepes, 10 mM $CaCl_2$, 0.2 M NaCl, 0.1% Brij 35, pH 7.5. Blood and plasma samples were assayed for fibrinogen concentration (normally in the range 2.5 to 4 mg/ml) and the concentration of fibrinogen adjusted comparably in the fibrinogen/buffer experiment.

Citrated human blood, plasma and fibrinogen (adjusted to comparable blood/plasma levels) were incubated with purified hementin (final concentration 10 units/ml) at 37° C. Care was taken to ensure that the hementin preparations were essentially free of an inhibitor of Factor Xa, which is known to contaminate impure preparations. Aliquots were removed at timed intervals, mixed with 2.5 NIH unit bovine thrombin and clotting time recorded.

In parallel experiments the snake fibrinogenolytic enzyme Atroxin was added to aliquots at the same timed intervals to test the integrity of fibrinogen (i.e. Atroxin will not result in a clot if fibrinogen has been previously acted upon by hementin). The results are as follows TT=thrombin clotting time; A=atroxin clotting time):

|  | Clotting time (sec) | | | | | |
| --- | --- | --- | --- | --- | --- | --- |
| Time | Control | 5 | 10 | 15 | 30 | 60 |
| Whole Blood | | | | | | |
| TT | 15 | >60 | >60 | >60 | >60 | >60 |
| A | 18 | 25 | >60 | >60 | >60 | >60 |
| Plasma | | | | | | |
| TT | 15 | 15 | 16 | 23 | 30 | >60 |
| A | 18 | 18 | 18 | 24 | 41 | >60 |
| Fibrinogen | | | | | | |
| TT | 10 | 10 | 10 | 10 | 10 | 10 |
| A | 20 | 20 | 20 | 20 | 20 | 20 |

The same results were obtained with platelet rich plasma (centrifugation of whole blood approximately 200×g for 10 min).

EXAMPLE 17

Rates of Deaggregation and Fibrinogenolysis by Hementin

Lyophilised hementin was reconstituted with isotonic saline before use for platelet studies or in 20 mM Hepes, 10 mM $CaCl_2$, 0.2 M NaCl, 0.1% Brij 35, pH 7.5 for in vitro assay. For the measurement of platelet aggregation, PRP was prepared ($300\pm50\times10^9$ platelets/l) from citrated venous blood of a human volunteer who had received neither medication nor alcohol for at least 2 weeks. Platelet aggregation studies were performed in a four channel aggregometer (Aggregcorder PA3210, Kyoto Daiichi Kagaku Co. Ltd, Japan) at 37 degrees Celsius.

Figure 11A:
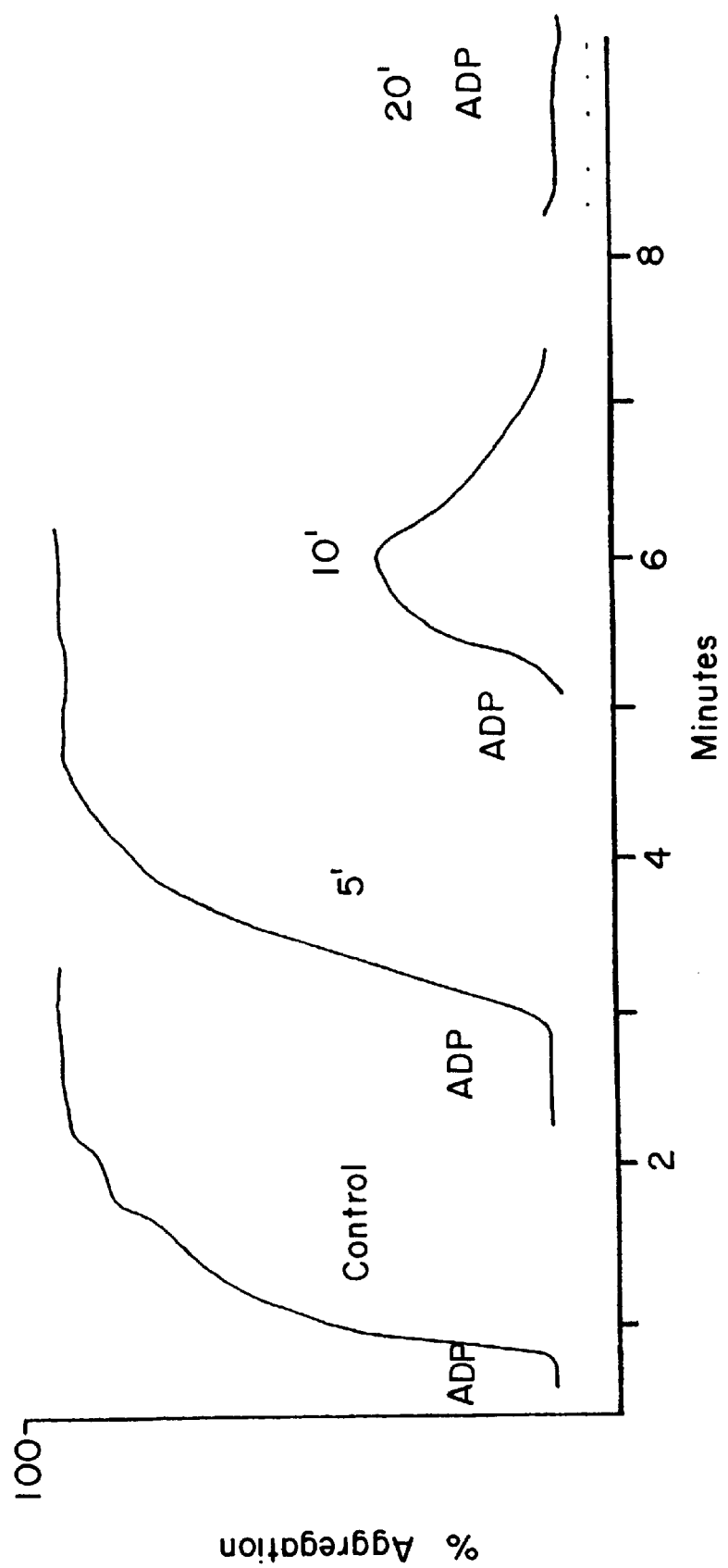
FIGS. 11A and 11B show platelet aggregation when platelet-rich plasma was pre-incubated with hementin (FIG. 11a), or when hementin was added after aggregates had formed (FIG. 11b).
Figure 11B:
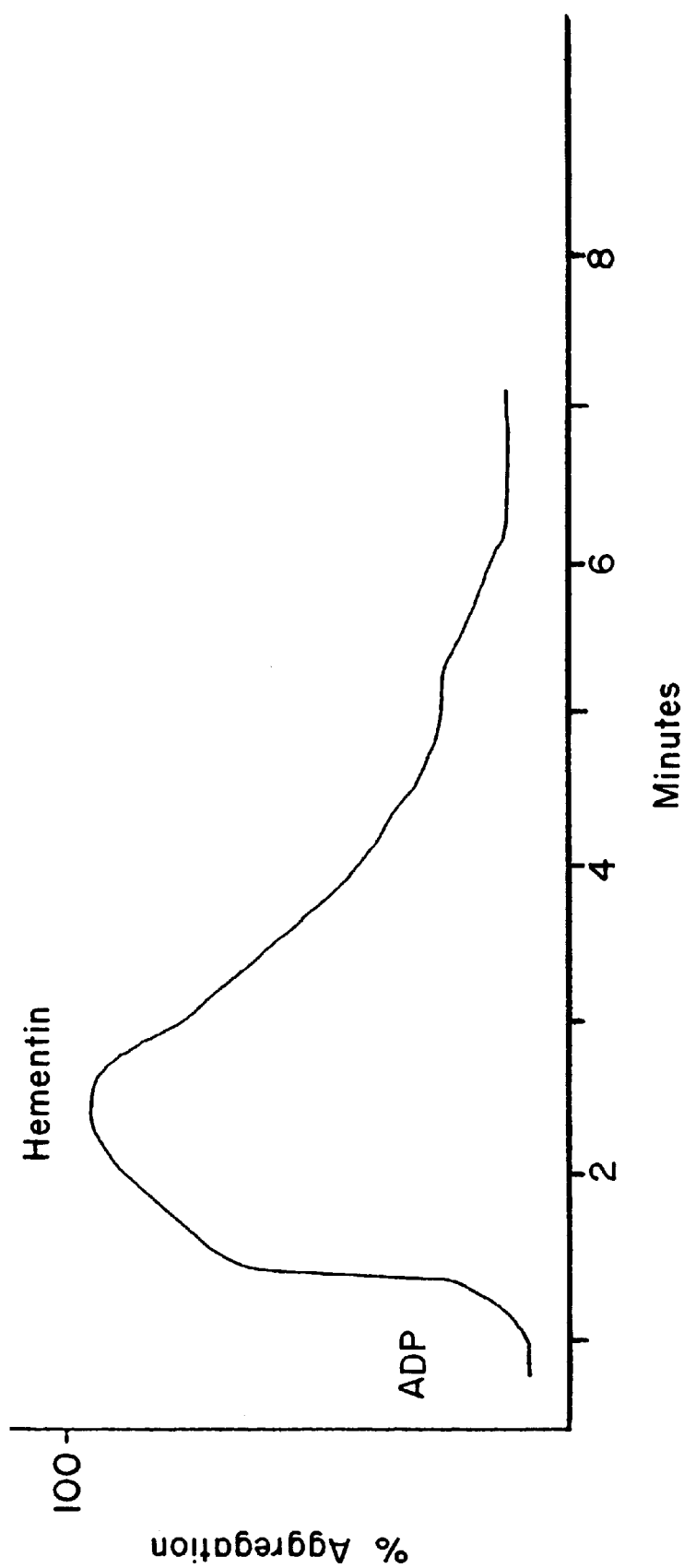

Platelet-rich plasma was pre-incubated at 37 degrees Celsius with purified hementin (10 units/ml) and ADP (2.5 um) added at 5, 10 and 20 minutes to determine platelet aggregability (results shown in FIG. 11a). The same PRP as (a) was aggregated with ADP (2.5 um) and hementin (10 units/ml) was added after peak aggregation was attained (results shown in FIG. 11b). Controls were also performed to confirm that sufficient ADP had been added to induce and maintain full aggregation over the entire period.

When PRP was incubated at 37 degrees Celsius with hementin (10 units/ml) coagulability with thrombin was lost after 10 minutes. When the ADP-aggregability of the same PRP preparation was also tested at times after addition of hementin (10 units/ml), the ability to aggregate was also lost after 10 minutes. In contrast, the time course of deaggregation induced by purified hementin (10 units/ml) upon preformed platelet aggregates (induced with 2.5 uM ADP) was much faster with deaggregation essentially complete 3 minutes after addition of hementin. The results are shown in FIG. 11. This action of hementin against platelets was complete before any significant effect on coagulation parameters could be measured. Control incubations in the absence of hementin remained fully aggregated.

These results suggest that hementin is able to break down the platelet-fibrinogen-platelet crosslinks faster than it is able to incoagulate plasma. This may be due to the unique cleavage site between the D and E domain of fibrinogen which may allow greater molecular accessibility to hementin than, for example, with plasmin cleavage sites which are predominantly in the carboxyl terminal of fibrinogen and which may be involved in binding to GpIIb-IIIa receptors. Consequently, hementin may be more selective for platelet bound fibrinogen than for free fibrinogen. Since platelet aggregates constitute the bulk of platelet-rich thrombi, which are refractory to current thrombolytic agents based on plasminogen activation, hementin therefore has clinical potential as an agent for deaggregation of platelets within platelet-rich clots causing subsequent thrombolysis.

EXAMPLE 18

Effect of Hementin on other Fibrinogen-Mediated Haematological Parameters

By virtue of its specific fibrinogenolytic action, purified hementin can be used to determine the contribution of fibrinogen to haematological parameters such as thrombin clotting times and activated partial thromboplastic time (APTT). In a similar manner, hementin can also be used to determine the fibrinogen contribution to the Erythrocyte Sedimentation Rate (ESR) which is a diagnostic marker for certain haematological disorders such as myeloma and rheumatoid arthritis.

Figure 12:
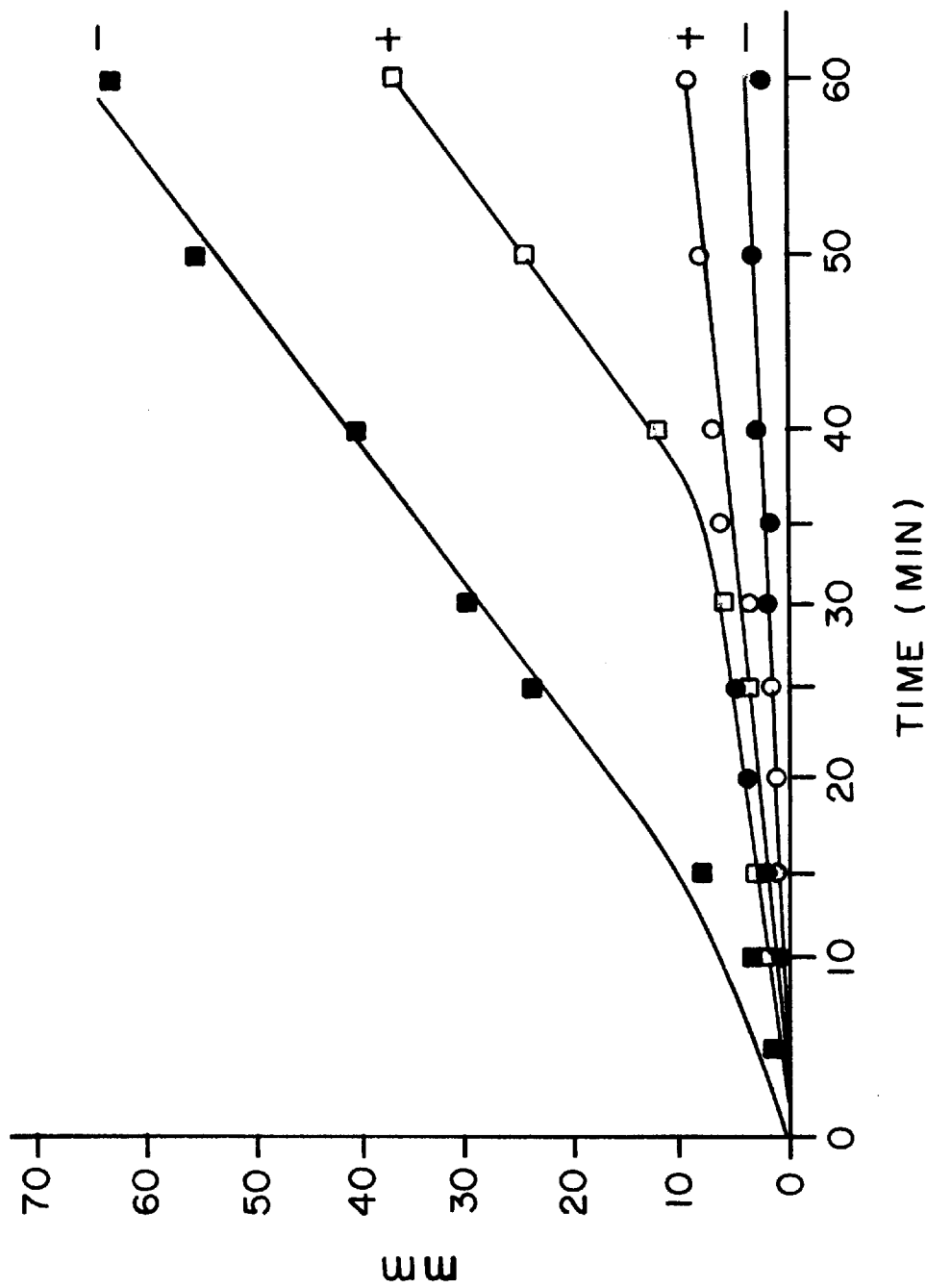
FIG. 12 shows the erythrocyte sedimentation rate (ESR) of plasma from a normal patient (circles) and one with a pulmonary embolism (squares), in the absence (open symbols) and presence (closed symbols) of hementin.

An exemplary experiment, summarised in FIG. 12, was carried out as follows. Citrated whole human blood from a volunteer (circles) was incubated for 1 h at 25 degrees Celsius (open circles) and without (closed circles) purified hementin (10 units/ml) and the ESR determined. The clotting parameters were determined at PT=95 s, APTT=340 s; TCT=99 s; Atroxin=146 s. The results indicate very little effect on ESR despite marked prolongation of clotting parameters for normal blood.

Citrated whole blood from a patient with pulmonary embolism (squares) was incubated for 1 h at 25 degrees Celsius with 35 units/ml hementin (open squares) and without purified hementin (closed squares) and the ESR determined. The results indicate that relative to normal values this patient's ESR was markedly accelerated. Incubation with hementin was able to partially reverse this effect leading to slower ESR.

In the example described above, hementin demonstrated marked quantifiable effects on ESR, suggesting that the accelerated ESR observed in patients with pulmonary embolism is in some way owing to erythrocyte interaction with fibrinogen such that the action of hementin leads to reduced ESR. Therefore, hementin can be used as a diagnostic index of the proportion of erythrocyte/fibrinogen in individual patients.

Moreover, hementin reversed the ESR towards normal levels, showing that hementin may be suitable as a therapeutic agent to address the causative factors of abnormal ESR.

Finally, in those cases where increased plasma fibrinogen affects blood viscosity, hementin can be used therapeutically to reduce viscosity. Increased fibrinogen levels in plasma can be raised acutely and chronically in certain diseased states, including infection, third trimester pregnancy, coagulation disorders, liver diseases, post-operative and with age. Reducing elevated fibrinogen levels can lead to reduced risk of clotting.

We claim:

1. A method for deaggregation of pre-formed platelet-rich thrombi in the course of thrombotic events, comprising contacting said platelet-rich thrombi with an amount of a pharmaceutical composition effective for deaggregating said thrombi, said composition comprising a polypeptide having the ability to deaggregate pre-formed platelet-rich thrombi with a specific activity of at least 1000 units/mg, wherein said polypeptide comprises the amino acid sequence

```
Thr Thr Leu Thr Glu Pro Glu Pro Xaa    (SEQ ID NO:2)
                 5

Leu Thr Xaa Leu Xaa Phe Val Xaa Xaa
10                  15

Val Xaa Xaa Xaa Met Pro Ile Phe Xaa
    20                  25

Met Ala Xaa Ala Xaa Ser Gln Ile Xaa
            30                  35

Xaa Xaa Phe,
``` wherein Xaa at position 9 consists of Pro, Phe, or Asn; Xaa at position 12 consists of Thr or Phe; Xaa at position 14 consists of Thr or Asn; Xaa at position 17 consists of Arg or Asp; Xaa at position 18 consists of Ile or Asn; Xaa at position 20 consists of Asn or Lys; Xaa at position 21 consists of Val or Leu; Xaa at position 22 consists of Glu or Asp; Xaa at position 27 consists of Val, Asp, Gly, Ala, or Phe; Xaa at position 30 consists of Thr or Arg; Xaa at position 32 consists of Asn or Gln; Xaa at position 36 consists of Thr or Tyr; Xaa at position 37 consists of Ser, Thr, or Tyr; and Xaa at position 38 consists of Thr or Lys.

2. The method of claim 1 wherein said polypeptide has a molecular mass of 80 kilodaltons.

3. The method of claim 1 wherein said effective amount comprises 20–100 units of said polypeptide per milliliter of blood of said patient, and said carrier comprises sterile saline.

4. The method of claim 1 further comprising an additional anticoagulant other than hementin.

5. A method for deaggregation of pre-formed platelet-rich thrombi in the course of thrombotic events, comprising contacting said platelet-rich thrombi with an amount of a pharmaceutical composition effective for deaggregating said thrombi, said composition comprising a polypeptide having the ability to deaggregate pre-formed platelet-rich thrombi with a specific activity of at least 1000 units/mg, wherein said polypeptide comprises the amino acid sequence

```
Thr Thr Leu Thr Glu Pro Gly Pro Phe Leu Thr Tyr Leu (SEQ ID NO:13) and
              5                   10

Thr Phe Val Xaa Ile Val Xaa Xaa Glu Met Pro Ile Phe
         15              20              25

Val Met Ala Thr Ala Asn Ser Gln Ile Thr Ser Thr
             30              35

Phe,
``` wherein Xaa at position 17 consists of Arg or Lys; Xaa at position 20 consists of Asn or Lys; and Xaa at position 21 consists of Val or Leu.

6. A method for deaggregation of pre-formed platelet-rich thrombi in the course of thrombotic events, comprising contacting said platelet-rich thrombi with an amount of a pharmaceutical composition effective for deaggregating said thrombi, said composition comprising a polypeptide having the ability to deaggregate pre-formed platelet-rich thrombi with a specific activity of at least 1000 units/mg, wherein said polypeptide comprises the amino acid sequence Gly Tyr Thr Asn Tyr Ala Lys Phe Leu Asp Tyr Leu Pro Val Glu (SEQ ID NO:11 position 1–15).

7. The method of claim 1, wherein said polypeptide is obtained by (a) homogenizing tissue from the salivary glands of the leech *Haementeria ghilianii* with buffers having salt concentrations from 15 to 25 mM and pHs from 7 to 8; and (b) purifying the homogenate by ion-exchange chromatography with an eluent having a salt concentration from 80 to 150 mM, and optionally by a gel filtration step.

8. The method of claim 7, wherein said homogenizing step is performed in a Hepes buffer; said ion-exchange chromatography employs sodium chloride as an eluent; and said polypeptide is protected by bovine serum albumin from inactivation upon freezing or lyophilization.

* * * * *

UNITED STATES PATENT AND TRADEMARK OFFICE
CERTIFICATE OF CORRECTION

PATENT NO. : 5,977,056
DATED : November 2, 1999
INVENTOR(S) : Christopher Powell-Jones It is certified that error appears in the above-identified patent and that said Letters Patent is hereby corrected as shown below:

Title page, [30] Foreign Application Priority Data, change filing date " Apr. 8, 1991" to -- Apr. 6, 1990--.

Signed and Sealed this

Eighth Day of August, 2000

Attest:

Q. TODD DICKINSON

*Attesting Officer*          *Director of Patents and Trademarks*

SEQUENCE LISTING

<160> NUMBER OF SEQ ID NOS: 13

<210> SEQ ID NO 1
<211> LENGTH: 10
<212> TYPE: PRT
<213> ORGANISM: Haementeria ghilianii

<400> SEQUENCE: 1

Thr Thr Leu Thr Glu Pro Glu Pro Asp Leu
 1               5                  10

<210> SEQ ID NO 2
<211> LENGTH: 39
<212> TYPE: PRT
<213> ORGANISM: Haementeria ghilianii
<220> FEATURE:
<221> NAME/KEY: VARIANT
<222> LOCATION: (9)
<223> OTHER INFORMATION: Xaa at position 9 equals Pro, Phe, or Asn
<220> FEATURE:
<221> NAME/KEY: VARIANT
<222> LOCATION: (12)
<223> OTHER INFORMATION: Xaa at position 12 equals Thr or Phe
<220> FEATURE:
<221> NAME/KEY: VARIANT
<222> LOCATION: (14)
<223> OTHER INFORMATION: Xaa at position 14 equals Thr or Asn
<220> FEATURE:
<221> NAME/KEY: VARIANT
<222> LOCATION: (17)
<223> OTHER INFORMATION: Xaa at position 17 equals Arg or Asp
<220> FEATURE:
<221> NAME/KEY: VARIANT
<222> LOCATION: (18)
<223> OTHER INFORMATION: Xaa at position 18 equals Ile or Asn
<220> FEATURE:
<221> NAME/KEY: VARIANT
<222> LOCATION: (20)
<223> OTHER INFORMATION: Xaa at position 20 equals Asn or Lys
<220> FEATURE:
<221> NAME/KEY: VARIANT
<222> LOCATION: (21)
<223> OTHER INFORMATION: Xaa at position 21 equals Val or Leu
<220> FEATURE:
<221> NAME/KEY: VARIANT
<222> LOCATION: (22)
<223> OTHER INFORMATION: Xaa at position 22 equals Glu or Asp
<220> FEATURE:
<221> NAME/KEY: VARIANT
<222> LOCATION: (27)
<223> OTHER INFORMATION: Xaa at position 27 equals Val, Asp, Gly, Ala,
      or Phe
<220> FEATURE:
<221> NAME/KEY: VARIANT
<222> LOCATION: (30)
<223> OTHER INFORMATION: Xaa at position 30 equals Thr or Arg
<220> FEATURE:
<221> NAME/KEY: VARIANT
<222> LOCATION: (32)
<223> OTHER INFORMATION: Xaa at position 32 equals Asn or Gln
<220> FEATURE:
<221> NAME/KEY: VARIANT
<222> LOCATION: (36)
<223> OTHER INFORMATION: Xaa at position 36 equals Thr or Tyr
<220> FEATURE:
<221> NAME/KEY: VARIANT
<222> LOCATION: (37)
<223> OTHER INFORMATION: Xaa at position 37 equals Ser, Thr, or Tyr
<220> FEATURE:
<221> NAME/KEY: VARIANT
<222> LOCATION: (38)
<223> OTHER INFORMATION: Xaa at position 38 equals Thr or Lys

<400> SEQUENCE: 2

-continued

```
Thr Thr Leu Thr Glu Pro Glu Pro Xaa Leu Thr Xaa Leu Xaa Phe Val
 1               5                  10                  15

Xaa Xaa Val Xaa Xaa Xaa Met Pro Ile Phe Xaa Met Ala Xaa Ala Xaa
            20                  25                  30

Ser Gln Ile Xaa Xaa Xaa Phe
            35
```

<210> SEQ ID NO 3
<211> LENGTH: 39
<212> TYPE: PRT
<213> ORGANISM: Haementeria ghilianii

<400> SEQUENCE: 3

```
Thr Thr Leu Thr Glu Pro Glu Pro Phe Leu Thr Tyr Leu Thr Phe Val
 1               5                  10                  15

Arg Ile Val Asn Val Glu Met Pro Ile Phe Val Met Ala Thr Ala Asn
            20                  25                  30

Ser Gln Ile Thr Ser Thr Phe
            35
```

<210> SEQ ID NO 4
<211> LENGTH: 39
<212> TYPE: PRT
<213> ORGANISM: Haementeria ghilianii

<400> SEQUENCE: 4

```
Thr Thr Leu Thr Glu Pro Glu Pro Phe Leu Thr Tyr Leu Thr Phe Val
 1               5                  10                  15

Arg Ile Val Asn Leu Glu Met Pro Ile Phe Val Met Ala Thr Ala Asn
            20                  25                  30

Ser Gly Ile Thr Ser Thr Phe
            35
```

<210> SEQ ID NO 5
<211> LENGTH: 39
<212> TYPE: PRT
<213> ORGANISM: Haementeria ghilianii

<400> SEQUENCE: 5

```
Thr Thr Leu Thr Glu Pro Glu Pro Phe Leu Thr Tyr Leu Thr Phe Val
 1               5                  10                  15

Arg Ile Val Lys Val Glu Met Pro Ile Phe Val Met Ala Thr Ala Asn
            20                  25                  30

Ser Gln Ile Thr Ser Thr Phe
            35
```

<210> SEQ ID NO 6
<211> LENGTH: 39
<212> TYPE: PRT
<213> ORGANISM: Haementeria ghilianii

<400> SEQUENCE: 6

```
Thr Thr Leu Thr Glu Pro Glu Pro Phe Leu Thr Tyr Leu Thr Phe Val
 1               5                  10                  15

Arg Ile Val Lys Leu Glu Met Pro Ile Phe Val Met Ala Thr Ala Asn
            20                  25                  30

Ser Gln Ile Thr Ser Thr Phe
            35
```

<210> SEQ ID NO 7
<211> LENGTH: 39

-continued

<212> TYPE: PRT
<213> ORGANISM: Haementeria ghilianii

<400> SEQUENCE: 7

Thr Thr Leu Thr Glu Pro Glu Pro Phe Leu Thr Tyr Leu Thr Phe Val
 1               5                  10                  15

Lys Ile Val Asn Val Glu Met Pro Ile Phe Val Met Ala Thr Ala Asn
            20                  25                  30

Ser Gln Ile Thr Ser Thr Phe
            35

<210> SEQ ID NO 8
<211> LENGTH: 39
<212> TYPE: PRT
<213> ORGANISM: Haementeria ghilianii

<400> SEQUENCE: 8

Thr Thr Leu Thr Glu Pro Glu Pro Phe Leu Thr Tyr Leu Thr Phe Val
 1               5                  10                  15

Lys Ile Val Asn Leu Glu Met Pro Ile Phe Val Met Ala Thr Ala Asn
            20                  25                  30

Ser Gln Ile Thr Ser Thr Phe
            35

<210> SEQ ID NO 9
<211> LENGTH: 39
<212> TYPE: PRT
<213> ORGANISM: Haementeria ghilianii

<400> SEQUENCE: 9

Thr Thr Leu Thr Glu Pro Glu Pro Phe Leu Thr Tyr Leu Thr Phe Val
 1               5                  10                  15

Lys Ile Val Lys Val Glu Met Pro Ile Phe Val Met Ala Thr Ala Asn
            20                  25                  30

Ser Gln Ile Thr Ser Thr Phe
            35

<210> SEQ ID NO 10
<211> LENGTH: 39
<212> TYPE: PRT
<213> ORGANISM: Haementeria ghilianii

<400> SEQUENCE: 10

Thr Thr Leu Thr Glu Pro Glu Pro Phe Leu Thr Tyr Leu Thr Phe Val
 1               5                  10                  15

Lys Ile Val Lys Leu Glu Met Pro Ile Phe Val Met Ala Thr Ala Asn
            20                  25                  30

Ser Gln Ile Thr Ser Thr Phe
            35

<210> SEQ ID NO 11
<211> LENGTH: 20
<212> TYPE: PRT
<213> ORGANISM: Haementeria ghilianii

<400> SEQUENCE: 11

Gly Tyr Thr Asn Tyr Ala Lys Phe Leu Asp Tyr Leu Pro Val Glu Arg
 1               5                  10                  15

Gly Ile Pro Leu
            20

```
<210> SEQ ID NO 12
<211> LENGTH: 10
<212> TYPE: PRT
<213> ORGANISM: Haementeria ghilianii

<400> SEQUENCE: 12

Glu Val Tyr Thr Asn Tyr Ala Ser Phe Leu
 1               5                  10

<210> SEQ ID NO 13
<211> LENGTH: 39
<212> TYPE: PRT
<213> ORGANISM: Haementeria ghilianii
<220> FEATURE:
<221> NAME/KEY: VARIANT
<222> LOCATION: (17)
<223> OTHER INFORMATION: Xaa at position 17 equals Arg or Lys
<220> FEATURE:
<221> NAME/KEY: VARIANT
<222> LOCATION: (20)
<223> OTHER INFORMATION: Xaa at position 20 equals Asn or Lys
<220> FEATURE:
<221> NAME/KEY: VARIANT
<222> LOCATION: (21)
<223> OTHER INFORMATION: Xaa at position 21 equals Val or Leu

<400> SEQUENCE: 13

Thr Thr Leu Thr Glu Pro Glu Pro Phe Leu Thr Tyr Leu Thr Phe Val
 1               5                  10                  15

Xaa Ile Val Xaa Xaa Glu Met Pro Ile Phe Val Met Ala Thr Ala Asn
            20                  25                  30

Ser Gln Ile Thr Ser Thr Phe
            35
```